(12) United States Patent
Sahin et al.

(10) Patent No.: US 11,920,194 B2
(45) Date of Patent: Mar. 5, 2024

(54) METHODS FOR CHARACTERIZING LOSS OF ANTIGEN PRESENTATION

(71) Applicants: BioNTech RNA Pharmaceuticals GmbH, Mainz (DE); TRON—Translationale Onkologie an der Universitätsmedizin der Johannes Gutenberg-Universität Mainzgemeinnützige GmbH, Mainz (DE)

(72) Inventors: Ugur Sahin, Mainz (DE); Martin Suchan, Mainz (DE); Barbara Schrörs, Mainz (DE); Martin Löwer, Mainz (DE); Petra Oehm, Mainz (DE)

(73) Assignees: BioNTech SE, Mainz (DE); TRON—Translationale Onkologie an der Universitätsmedizin der Johannes Gutenberg-Universität Mainz, Mainz (DE)

( * ) Notice: Subject to any disclaimer, the term of this patent is extended or adjusted under 35 U.S.C. 154(b) by 179 days.

(21) Appl. No.: 16/619,761

(22) PCT Filed: Jun. 1, 2018

(86) PCT No.: PCT/EP2018/064479
§ 371 (c)(1),
(2) Date: Dec. 5, 2019

(87) PCT Pub. No.: WO2018/224406
PCT Pub. Date: Dec. 13, 2018

(65) Prior Publication Data
US 2020/0140945 A1    May 7, 2020

(30) Foreign Application Priority Data
Jun. 9, 2017  (WO) ................. PCT/EP2017/064112

(51) Int. Cl.
*C12Q 1/68* (2018.01)
*C12Q 1/686* (2018.01)
*C12Q 1/6876* (2018.01)

(52) U.S. Cl.
CPC ........... *C12Q 1/6876* (2013.01); *C12Q 1/686* (2013.01); *C12Q 2600/156* (2013.01)

(58) Field of Classification Search
CPC ................. C12Q 1/6876; C12Q 1/686; C12Q 2600/156; C12Q 1/6886
See application file for complete search history.

(56) References Cited

U.S. PATENT DOCUMENTS

2003/0119017 A1*  6/2003  McSwiggen ....... C12N 15/1137
                                                                        435/6.18
2015/0322507 A1* 11/2015  Zimmermann ......... C12Q 1/68
                                                                        506/2
(Continued)

FOREIGN PATENT DOCUMENTS

WO    WO 2018/224406 A1    12/2018

OTHER PUBLICATIONS

Paschen et al. The coincidence of chromosome 15 aberrations and beta-2-microglobulin gene mutations is causative for the total loss of human leukocyte antigen class I expression in melanoma. Clin Cancer Research, vol. 12(11), p. 3297-3305, 2006.*

(Continued)

*Primary Examiner* — Stephanie K Mummert
(74) *Attorney, Agent, or Firm* — Neal, Gerber & Eisenberg LLP

(57) ABSTRACT

This invention relates to methods for screening for a genotype for loss of antigen presentation via MHC class I in a subject and/or respectively detecting a subject's increased (Continued)

Figure 1:
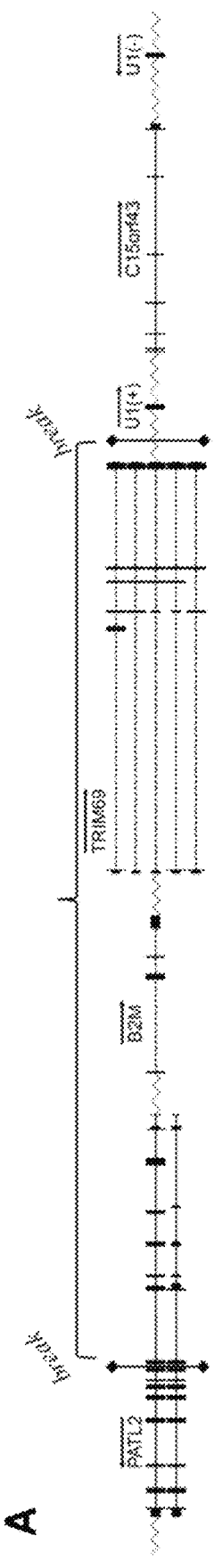
Figure 1:
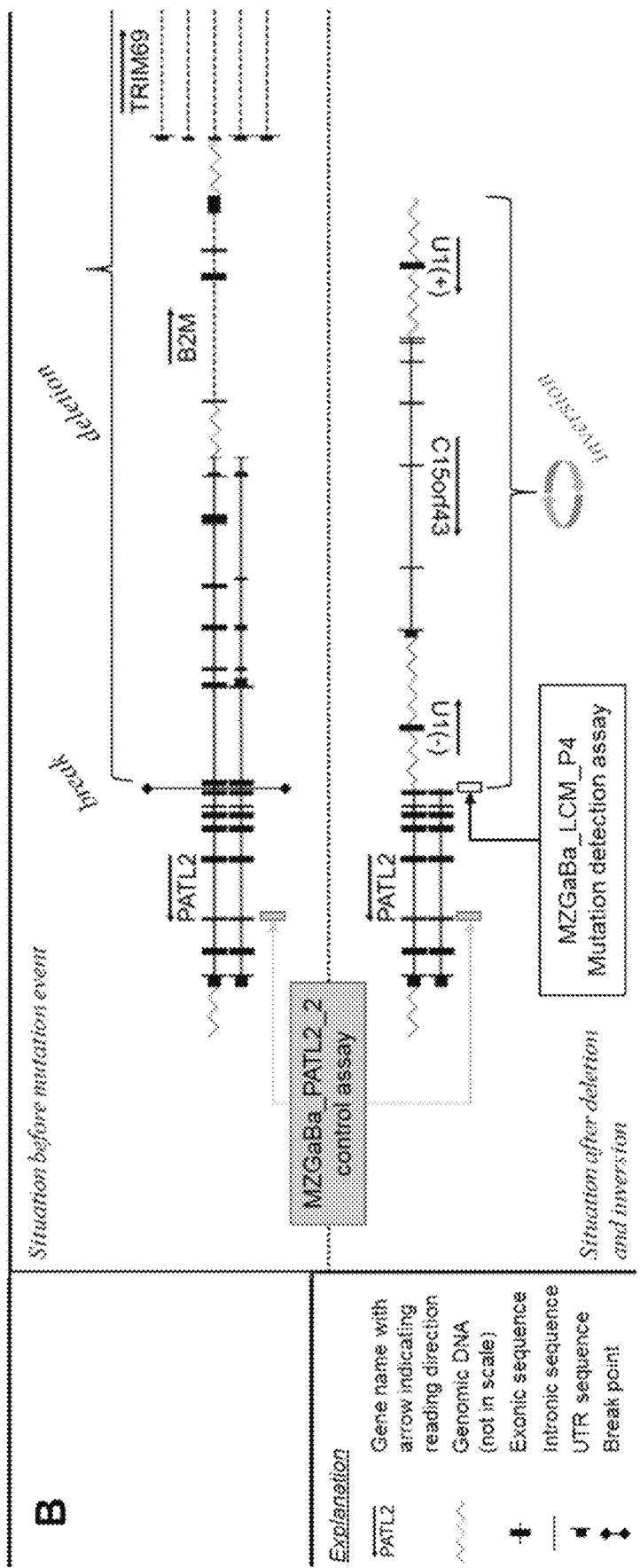

risk of resistance against immunotherapy such as against vaccination.

23 Claims, 4 Drawing Sheets

Specification includes a Sequence Listing.

(56) References Cited

U.S. PATENT DOCUMENTS

2015/0361451 A1* 12/2015 Le Fourn .............. C12N 15/85
435/375
2018/0141992 A1* 5/2018 Cowan .................. C12N 15/11

OTHER PUBLICATIONS

Jordanova, ES, et al. Beta 2-microglobulin aberrations in diffuse large B-cell lymphoma of the testis and central nervous system. Int. J. Cancer, vol. 103, p. 393-398, (2003).*
Paschen et al. (Int J of Cancer, 2003, vol. 103, p. 759-767) (Year: 2003).*
Bernal et al., *Cancer Immunol. Immunother.*, 61: 1359-1371 (2012).
D'Urso et al., *Journal of Clinical Investigation, American Society for Clinical Investigation*, 87: 284-292 (1991).
Paschen et al., *Int. J. Cancer*, 103: 759-767 (2003).
Paschen et al., *Clin. Cancer Res.*, 12(11): 3297-3305 (2006).
European Patent Office, International Search Report in International Application No. PCT/EP2018/064479 (dated Jun. 27, 2018).
European Patent Office, Written Opinion in International Application No. PCT/EP2018/064479 (dated Jun. 27, 2018).

* cited by examiner

A

B

Figure 3

Fusion sequence (reverse complement of sequence 02 positions 356-461) with inserted thymidine base (SEQ ID NO: 8)

CCACCCAGAAGGAAACAAGCAAAGAAATCTCCAAGGGACCACAAAAAACCCGCTAT
AGGTT | T TCTTCTCATGCAGTGGTCCGAATCGAGGGTTCCCTGGGCCAGGTA

*Explanation*

„CACCC..." = chr15:45,304,565 – chr15:45,304,626
| T = breakpoint with inserted thymidine base
„TCTTC..." = chr15:44,962,085 – chr15:44,962,041 (PATL2)

Fusion sequence with binding sites for primers and probe (SEQ ID NO: 17)

CCACCCAGAAGGAAACAAGCAAAGAAATCTCCAAGGGACCACAAAAAACCCGCTAT
AGGTTTCTTCCATGCA...

Oligos used for TaqMan® assay MZGaBa_LCM_P4_FRP

| Oligo name | Oligonucleotide sequence (5'-3' direction) | length [bp] |
|---|---|---|
| MZGaBa_LCM P4_F | ████████████████ (SEQ ID NO: 18) | 94 |
| MZGaBa_LCM P4_R | CCACCCAGAAGGAAACAAGC (SEQ ID NO: 19) | |
| MZGaBa_LCM P4_P | (FAM)-CAAGGGACCACAAAAAACCCGCTATAGGTTTCTTC-(BHQ1) (SEQ ID NO: 20) | |

Figure 4

Fusion sequence (reverse complement of sequence 02 positions 356-461) with inserted thymidine base (SEQ ID NO: 8)

CCACCCAGAAGGAAACAAGCAAAGAAATCTCCAAGGGACCACAAAAAACCGCTAT
AGGTT |T̲ TCTTCTCATGCAGTGGTCCGAATCGAGGGTTCCCTGGGCCAGTA

*Explanation*

„CACCC..." = chr15:45304565 – chr15:45304626
|T̲ = breakpoint with inserted thymidine base
„TCTTC..." = chr15:44962085 – chr15:44962041 (PATL2)

Fusion sequence with binding sites for primers and probe (SEQ ID NO: 21)

▓▓▓▓▓▓▓▓▓▓▓▓▓▓▓▓▓▓▓▓▓▓▓▓-CACAAAAACCCGCTATAGGTTTTCTTCTCAT
GCAGTGGTCCGAATCGAGGGTTCCCTGGGCCA

Oligos used for TaqMan® assay "MZGaBa_MaSu_m_FRP")

| Oligo name | Oligonucleotide sequence (5'-3' direction) | length [bp] |
|---|---|---|
| MZGaBa_Ma Su_m_F | ▓▓▓▓▓▓▓▓▓▓▓▓▓▓▓▓▓▓▓ (SEQ ID NO: 22) | |
| MZGaBa_Ma Su_m_R | ▓▓▓▓▓▓▓▓▓▓▓▓▓▓▓ (SEQ ID NO: 23) | 98 |
| MZGaBa_Ma Su_m_P | (FAM)-▓CACAAAAACCCGCTATAGGTTTTCTTCTCATGCAG▓-(BHQ1) (SEQ ID NO: 24) | |

METHODS FOR CHARACTERIZING LOSS OF ANTIGEN PRESENTATION

TECHNICAL FIELD OF THE INVENTION

This invention relates to methods for screening for a genotype for loss of antigen presentation via MHC class I in a subject and/or respectively detecting a subject's increased risk of resistance against immunotherapy such as against vaccination.

BACKGROUND OF THE INVENTION

The immune system plays an important role in defense against microorganisms, for example viruses, fungi and bacteria, as well as in recognizing and repelling malignant cells (tumor cells). The evolution of the immune system resulted in a highly effective network based on two types of defense: the innate and the adaptive immunity. In contrast to the evolutionary ancient innate immune system that relies on invariant receptors recognizing common molecular patterns associated with pathogens, the adaptive immunity is based on highly specific antigen receptors on B cells (B lymphocytes) and T cells (T lymphocytes) and clonal selection. While B cells raise humoral immune responses by secretion of antibodies, T cells mediate cellular immune responses leading to destruction of recognized cells.

T cells play a central role in cell-mediated immunity in humans and animals. The recognition and binding of a particular antigen is mediated by the T cell receptors expressed on the surface of T cells. The T cell receptor (TCR) of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector r cell. To be able to target a vast variety of antigens, the T cell receptors need to have a great diversity.

MHC (major histocompatibility complex) class I molecules consist of a membrane-bound heavy chain and non-covalently linked beta-2-microglobulin (B2M). Hetero-dimerization of the MHC class I heavy chain with B2M is essential for stable cell surface expression of MHC class I molecules (Bjorkman P J et al., 1987, Nature 329, 506-12; D'Urso C M et al., 1991, J Clin Invest. 87, 284-92). On the cell surface, MHC class 1 molecules present intracellularly processed peptides to the immune system, which allows to distinguish between self and foreign, healthy and infected or normal and tumor.

Antigen-specific immunotherapy aims to enhance or induce specific immune responses in patients to control infectious or malignant diseases. Cells presenting immunogenic peptides derived from pathogen- and tumor-associated antigens can be specifically targeted by active or passive immunization strategies. Active immunization tends to induce and expand antigen-specific T cells in the patient, which are able to specifically recognize and kill diseased cells. In contrast, passive immunization relies on the adoptive transfer of T cells, which were expanded and optional genetically engineered in vitro (adoptive T cell therapy; ACT).

Vaccines aim to induce endogenous antigen-specific immune responses by active immunization. Different antigen formats can be used for vaccination including whole diseased cells, proteins, peptides or immunizing vectors such as RNA, DNA or viral vectors that can be applied either directly in vivo or in vitro by pulsing of dendritic cells (DCs) following transfer into the patient.

ACT based immunotherapy can be broadly defined as a form of passive immunization with previously sensitized T cells that are transferred to non-immune recipients or to the autologous host after ex vivo expansion from low precursor frequencies to clinically relevant cell numbers. An approach overcoming the limitations of ACT is the adoptive transfer of autologous T cells reprogrammed to express an antigen-reactive TCR of defined specificity during short-time ea vivo culture followed by reinfusion into the patient.

Further immunotherapeutic strategies include immuno-regulatory monoclonal antibodies aimed at blocking inhibitory or boosting stimulatory immune signalling.

Immunotherapy such as cancer immunotherapy aiming to activate T cell-mediated immune responses has achieved clear clinical responses. However, only a fraction of patients responds to treatment and there is an urgent call for characterization of predictive biomarkers. Current progress in the field of immunotherapy such as cancer immunotherapy is based on the capacity of T cells to kill diseased cells such as cancer cells that present antigen such as tumor antigen in the context on a MHC class I molecule. However, immunotherapy building on CD8 T cells will be futile in patients harboring MHC class I negative or deficient cells. It is therefore mandatory to explore if these important molecules for T cell cytotoxicity are expressed by target cells such as cancer target cells.

The absence or inactivation of B2M directly implies loss of antigen presentation via MHC class I. This is a known tumor immune escape mechanism and is associated with resistances against immunotherapy (Zaretsky J M, et al., 2016, N Engl J Med. 375, 819-29). Even small B2M-negative tumor subpopulations can outgrow under the selective pressure of an immunotherapeutic treatment leading to disease progression or relapse. Thus, B2M-loss represents a relevant biomarker for secondary resistances against immunotherapy and its monitoring is advisable.

The present invention identifies a chromosomal deletion and inversion event in chromosome 15 resulting in B2M deletion. Furthermore, assays are established according to the present invention which are suitable for the detection of this deletion/inversion event.

DESCRIPTION OF INVENTION

Summary of the Invention

In one aspect, the invention relates to a method for screening for a genotype for loss of antigen presentation via MHC class I, comprising: obtaining a sample containing nucleic acid from a subject, and identifying a chromosomal deletion and inversion event in a chromosome 15, wherein the deletion and inversion event results in the loss of the beta-2-microglobulin (B2M) locus, and wherein the presence of the chromosomal deletion and inversion event indicates that the subject possesses a genotype for loss of antigen presentation via MHC class I.

In one embodiment, identifying a chromosomal deletion and inversion event in a chromosome 15 comprises detecting the presence or absence of a nucleic acid sequence comprising a sequence selected from the group consisting of:
  (i) a sequence identifying a chromosomal deletion and inversion event in a chromosome 15, wherein the deletion and inversion event results in the loss of the beta-2-microglobulin (B2M) locus, and comprising the sequence set forth in SEQ ID NO: 9 (AGGTT(T)nTCTTC, wherein n is an integer from 0 to 5, preferably 0 or 1), the sequence set forth in SEQ ID NO: 9 surrounding the end point of the deletion, which is the start point of the inverted region, (ii) the sequence set forth in SEQ ID NO: 17 (CCACCCAGAAGGAAACAAGCAAAGAAATCTCCAAGGGACCACAAAAAACCCGCTATAGGTTTCTTCTCATGCAGTGGTCCGAATCGAGGGTTC) or a portion thereof of at least 40 nucleotides comprising the sequence set forth in SEQ ID NO: 10 (AGGTTTTCTTC), (iii) the sequence set forth in SEQ ID NO: 21 (CAAGCAAAGAAATCTCCAAGGGACCACAAAAAACCCGCTATAGGTTTTCTTCTCATGCAGTGGTCCGAATCGAGGGTTCCCTGGGCCA) or a portion thereof of at least 40 nucleotides comprising the sequence set forth in SEQ ID NO: 10 (AGGTTTTCTTC), (iv) a sequence complementary to the sequences set forth in any one of (i) to (iii), and (v) a sequence which is at least 90% identical to the sequences set forth in any one of (i) to (iv), wherein detection of the nucleic acid sequence indicates the presence of a chromosomal deletion and inversion event in a chromosome 15 that is predictive of a genotype for loss of antigen presentation via MHC class I.

In one embodiment, identifying a chromosomal deletion and inversion event in a chromosome 15 comprises amplifying a nucleic acid sequence comprising a sequence selected from the group consisting of:

(i) a sequence identifying a chromosomal deletion and inversion event in a chromosome 15, wherein the deletion and inversion event results in the loss of the beta-2-microglobulin (B2M) locus, and comprising the sequence set forth in SEQ ID NO: 9 (AGGTT(T)nTCTTC, wherein n is an integer from 0 to 5, preferably 0 or 1), the sequence set forth in SEQ ID NO: 9 surrounding the end point of the deletion, which is the start point of the inverted region, (ii) the sequence set forth in SEQ ID NO: 17 (CCACCCAGAAGGAAACAAGCAAAGAAATCTCCAAGGGACCACAAAAAACCCGCTATAGGTTTCTTCTCATGCAGTGGTCCGAATCGAGGGTTC) or a portion thereof of at least 40 nucleotides comprising the sequence set forth in SEQ ID NO: 10 (AGGTTTCTrC), (iii) the sequence set forth in SEQ ID NO: 21 (CAAGCAAAGAAATCTCCAAGGGACCACAAAAAACCCGCTATAGGTTTTCTTCTCATGCAGTGGTCCGAATCGAGGGTTCCCTGGGCCA) or a portion thereof of at least 40 nucleotides comprising the sequence set forth in SEQ ID NO: 10 (AGGTTTTCTTC), (iv) a sequence complementary to the sequences set forth in any one of (i) to (iii), and (v) a sequence which is at least 90%1 identical to the sequences set forth in any one of (i) to (iv).

In one embodiment, the amplification is performed using primers comprising the sequences set forth in SEQ ID NO: 18 (5'-GAACCCTCGATTCGGACCAC-3'), and SEQ ID NO: 19 (5'-CCACCCAGAAGGAAACAAGC-3').

In one embodiment, the amplification is performed using primers comprising the sequences set forth in SEQ ID NO: 22 (5'-CAAGCAAAGAAATCTCCAAGGGA-3'), and SEQ ID NO: 23 (5'-TGGCCCAGGGAACCCTC-3').

In a further aspect, the invention relates to a method for screening for a genotypc for loss of antigen presentation via MHC class I, by identifying a chromosomal deletion and inversion event in a chromosome 15 resulting in the loss of the beta-2-microglobulin (B2M) locus comprising: obtaining a sample containing nucleic acid from a subject, hybridizing to the nucleic acid the group of primers comprising the sequences set forth in SEQ II) NO: 15 (5'-AGCATGTCGACACAGCTACC-3'), and SEQ ID NO: 16 (5'-ACCTCTCAGCTTACCCCCAT-3'), amplifying the hybridized group of primers, and detecting the presence or absence of an amplification product, wherein detection of the amplification product indicates the presence of a chromosomal deletion and inversion event in a chromosome 15 resulting in the loss of the beta-2-microglobulin (B2M) locus that is predictive of a genotype for loss of antigen presentation via MHC class I.

In one embodiment, the amplification product has a length of 160 to 200 bp, preferably 170 to 190 bp, more preferably about 180 bp.

In a further aspect, the invention relates to a method for screening for a genotype for loss of antigen presentation via MHC class I, by identifying a chromosomal deletion and inversion event in a chromosome 15 resulting in the loss of the beta-2-microglobulin (B2M) locus comprising: obtaining a sample containing nucleic acid from a subject, hybridizing to the nucleic acid the group of primers comprising the sequences set forth in SEQ ID NO: 18 (5'-GAACCCTCGATTCGGACCAC-3'), and SEQ ID NO: 19 (5'-CCACCCAGAAGGAAACAAGC-3'), amplifying the hybridized group of primers, and detecting the presence or absence of an amplification product, wherein detection of the amplification product indicates the presence of a chromosomal deletion and inversion event in a chromosome 15 resulting in the loss of the beta-2-microglobulin (B2M) locus that is predictive of a genotype for loss of antigen presentation via MHC class 1.

In one embodiment, the amplification product has a length of 80 to 100 bp, preferably 90 to 95 bp, more preferably about 94 bp. The sequence of a preferred amplification product is set forth in SEQ ID NO: 17.

In one embodiment, the method further compriscs hybridizing to the nucleic acid a probe comprising the sequence set forth in SEQ ID NO: 20 (5'-CAAGGGACCACAAAAAACCCGCTATAGGTTTTCTTC-3') or a sequence complementary to SEQ ID NO: 20. In one embodiment, the probe is a TaqMan probe.

In a further aspect, the invention relates to a method for screening for a genotype for loss of antigen presentation via MHC class 1, by identifying a chromosomal deletion/inversion in a chromosome 15 resulting in the loss of the beta-2-microglobulin (B2M) locus comprising: obtaining a sample containing nucleic acid from a subject, hybridizing to the nucleic acid the group of primers comprising the sequences set forth in SEQ ID NO: 22 (5'-CAAGCAAAGAAATCTCCAAGGGA-3'), and SEQ ID NO: 23 (5'-TGGCCCAGGGAACCCTC-3'), amplifying the hybridized group of primers, and detecting the presence or absence of an amplification product, wherein detection of the amplification product indicates the presence of a chromosomal deletion and inversion in a chromosome 15 resulting in the loss of the beta-2-microglobulin (B2M) locus that is predictive of a genotype for loss of antigen presentation via MHC class 1.

In one embodiment, the amplification product has a length of 80 to 95 bp, preferably 85 to 90 bp, more preferably about 88 bp. The sequence of a preferred amplification product is set forth in SEQ ID NO: 21.

In one embodiment, the method further comprises hybridizing to the nucleic acid a probe comprising the sequence set forth in SEQ ID NO: 24 (5'-CACAAAAAACCCGCTAr-AGGrrTCTTCTCArGCAGT-3') or a sequence complementary to SEQ ID NO: 24. In one embodiment, the probe is a TaqMan probe.

In one embodiment of the method of all aspects of the invention, the deletion starts after position chr15:44,962,085 and ends at position chr15:45,166,582.

In one embodiment of the method of all aspects of the invention, the inversion comprises an inversion of the sequence downstream of the deleted region and follows the deletion.

In one embodiment of the method of all aspects of the invention, the inverted region starts at position chr15:45,166,583 and ends at position chr15:45,304,626.

In one embodiment of the method of all aspects of the invention, the sequence surrounding the end point of the deletion, which is the start point of the inverted region comprises the sequence set forth in SEQ ID NO: 9 (AGGTT(T)nTCTTC, wherein n is an integer from 0 to 5, preferably 0 or 1 or a sequence complementary to SEQ ID NO: 9.

In one embodiment of the method of all aspects of the invention, identifying a chromosomal deletion and inversion event, detecting the presence or absence of a nucleic acid sequence and/or amplifying a nucleic acid sequence or a hybridized group of primers comprises performing polymerase chain reaction (PCR). In one embodiment, the PCR is quantitative real-time PCR (qRT-PCR).

In one embodiment of the method of all aspects of the invention, the loss of antigen presentation via MHC class I indicates resistance against immunotherapy. In one embodiment, the immunotherapy is tumor immunotherapy.

In a further aspect, the invention relates to a kit comprising means for detecting the presence or absence of and/or for amplifying a nucleic acid sequence comprising a sequence selected from the group consisting of:
(i) a sequence identifying a chromosomal deletion and inversion event in a chromosome 15, wherein the deletion and inversion event results in the loss of the beta-2-microglobulin (B2M) locus, and comprising the sequence set forth in SEQ ID NO: 9 (AGGTT(T)nTCTTC, wherein n is an integer from 0 to 5, preferably 0 or 1), the sequence set forth in SEQ ID NO: 9 surrounding the end point of the deletion, which is the start point of the inverted region,
(ii) the sequence set forth in SEQ ID NO: 17 (CCACCCAGAAGGAAACAAGCAAAGAAATCTCCAAGGGACCACAAAAAACCCGCTATAGGTTTTCTTCT-CATGCAGTGGTCCGAATCGAGGGTTC) or a portion thereof of at least 40 nucleotides comprising the sequence set forth in SEQ ID NO: 10 (AGGTTTTCTTC),
(iii) the sequence set forth in SEQ ID NO: 21 (CAAGCAAAGAAATCTCCAAGGGAC-CACAAAAAACCCGCTATAGGTTTTCTTCTCATGCAGTGGTCCGAATCGAGGGTTCCCTGGGC-CA) or a portion thereof of at least 40 nucleotides comprising the sequence set forth in SEQ II) NO: 10 (AGGrTTCTTC).
(iv) a sequence complementary to the sequences set forth in any one of (i) to (iii), and
(v) a sequence which is at least 90% identical to the sequences set forth in any one of (i) to (iv).

In one embodiment, the kit comprises primers comprising the sequences set forth in SEQ ID NO: 18 (5'-GAACCCTC-GATTCGGACCAC-3'), and SEQ ID NO: 19 (5'-CCACCCAGAAGGAAACAAGC-3').

In one embodiment, the kit comprises primers comprising the sequences set forth in SEQ ID NO: 22 (5'-CAAGCAAAGAAATCTCCAAGGGA-3'), and SEQ ID NO: 23 (5'-TGGCCCAGGGAACCCTC-3').

In a further aspect, the invention relates to a kit comprising the group of primers comprising the sequences set forth in SEQ ID NO: 15(5'-AGCATGTCGACACAGCTACC-3'), and SEQ ID NO: 16 (5'-ACCTCTCAGCTTACCCCCAT-3').

In a further aspect, the invention relates to a kit comprising the group of primers comprising the sequences set forth in SEQ ID NO: 18 (5'-GAACCCTCGATTCGGACCAC-3'), and SEQ ID NO: 19 (5'-CCACCCAGAAGGAAACAAGC-3').

In one embodiment, the kit further comprises a probe comprising the sequence set forth in SEQ ID NO: 20 (5'-CAAGGGACCACAAAAAACCCGC-TATAGGTTTTCTTC-3') or a sequence complementary to SEQ ID NO: 20. In one embodiment, the probe is a raqMan probe.

In a further aspect, the invention relates to a kit comprising the group of primers comprising the sequences set forth in SEQ ID NO: 22 (5'-CAAGCAAAGAAATCTC-CAAGGGA-3'), and SEQ ID NO: 23 (5'-TGGCCCAGG-GAACCCTC-3').

In one embodiment, the kit further comprises a probe comprising the sequence set forth in SEQ ID NO: 24 (5'-CACAAAAAACCCGCTATAGGTTTTCTTCT-CATGCAGT-3') or a sequence complementary to SEQ ID NO: 24. In one embodiment, the probe is a TaqMan probe.

In one embodiment, the kit further comprises instructions for use of the kit for identifying a chromosomal deletion and inversion event in a chromosome 15.

In one embodiment, the kit further comprises means for performing polymerase chain reaction (PCR). In one embodiment, the PCR is quantitative real-time PCR (qRT-PCR).

According to a particular embodiment, the methods of the invention as defined herein are in vitro methods, performed on a sample removed from the body of a subject.

Another aspect relates to a method for treating a subject, in particular by immunotherapy, e.g., by inducing an immune response in a subject, comprising screening a subject for a genotype for loss of antigen presentation via MHC class I according to the methods of the invention and, if the subject does not possess a genotype for loss of antigen presentation via MHC class I, administering to the subject an immunotherapeutic agent such as a vaccine.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", *H. G. W. Leuenberger. B. Nagel. and H. Kölbl. Eds.*, (1995) *Helvetica Chimica Acta*, C1-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual, 2nd Edition*, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e., the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention The present invention broadly relates to the immunotherapy of diseases, in particular cancer diseases, by utilizing a protein or a protein fragment present in diseased cells as a label for and targeting diseased cells. In particular, the diseased cells may be targeted by targeting a fragment of an antigen presented on the surface of the diseased cells in the context of MHC. The immunotherapy according to the present invention may be effected by means of active and/or passive immunotherapeutic approaches.

Specifically, the present invention aims at defining whether a subject is suitable for immunotherapy or continues to be suitable for immunotherapy by screening for a genotype for loss of antigen presentation via MHC class I by identifying a chromosomal deletion and inversion event in a chromosome 15 resulting in the loss of the beta-2-microglobulin (B2M) locus. Identifying a chromosomal deletion and inversion event in a chromosome 15 resulting in the loss of the beta-2-microglobulin (B2M) locus is predictive of a genotype for loss of antigen presentation via MHC class I and of the subject not being suitable for immunotherapy. Not identifying a chromosomal deletion and inversion event in a chromosome IS resulting in the loss of the beta-2-microglobulin (B2M) locus is predictive of the subject being suitable for immunotherapy. If a subject has been treated with immunotherapy in the past or is currently being treated with immunotherapy, a chromosomal deletion and inversion event in a chromosome 15 resulting in the loss of the beta-2-microglobulin (B2M) locus may result in a resistance towards immunotherapy. Accordingly, identifying a chromosomal deletion and inversion event in a chromosome 15 resulting in the loss of the beta-2-microglobulin (B2M) locus is predictive of a genotype for loss of antigen presentation via MHC class I and of the subject not being suitable any longer for immunotherapy. Not identifying a chromosomal deletion and inversion event in a chromosome 15 resulting in the loss of the beta-2-microglobulin (B2M) locus is predictive of the subject still being suitable for immunotherapy.

According to the invention, the term "immunotherapy" relates to the treatment of disease by inducing or enhancing an immune response, in particular a T cell mediated immune response. Preferably, the immune response is a cellular immune response targeting (abnormal) antigens presented on the surface of diseased cells such as tumor or cancer cells in the context of MHC molecules. The term "immunotherapy" includes antigen immunization or antigen vaccination, or tumor immunization or tumor vaccination.

An antigen or a fragment thereof (optionally as part of a larger polypeptide comprising the fragment) suitable for immunotherapy or a nucleic acid coding for the antigen or fragment (optionally as part of a larger polypeptide comprising the fragment) may be used as a vaccine in order to enhance or induce an immune response against the antigen or a fragment thereof, in particular by inducing and/or activating appropriate effector cells such as T cells that recognize the antigen or a fragment thereof (in particular when presented in the context of MHC) through an appropriate receptor (such as T cell receptor or artificial T cell receptor). Alternatively or additionally, effector cells such as T cells that recognize the antigen or a fragment thereof (in particular when presented in the context of MHC) through an appropriate receptor (such as T cell receptor or artificial T cell receptor) may be administered. Without wishing to be bound to a particular theory, it is believed that the antigen or a fragment thereof has a high likelihood of being taken up by antigen presenting cells and being presented by the antigen presenting cells, thus ultimately resulting in an efficient immune response against diseased cells expressing the antigen or a fragment thereof.

The term "immune response" relates to a reaction of the immune system, preferably to an antigen, and preferably refers to a cellular immune response, a humoral immune response, or both. An immune response may be protective/preventive/prophylactic and/or therapeutic. According to the invention, the term "immune response to" or "immune response against" with respect to a target such as an antigen, cell or tissue, relates to an immune response directed against the target.

It is preferred that the immune response induced by the compositions described herein comprises the steps of activation of antigen presenting cells, such as dendritic cells and/or macrophages, presentation of an antigen or fragment thereof by said antigen presenting cells and activation of cytotoxic T cells due to this presentation.

"Inducing an immune response" may mean that there was no immune response before induction, but it may also mean that there was a certain level of immune response before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor-expressed antigen may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

The terms "cellular immune response", "cellular response", "cell-mediated immunity" or similar terms are meant to include a cellular response directed to cells characterized by expression of an antigen and/or presentation of an antigen with MHC class I and/or class II. The cellular response relates to cells called T cells or T lymphocytes which act as either "helpers" or "killers". The helper T cells (also termed CD4+ T cells) play a central role by regulating the immune response and the killer cells (also termed cytotoxic T cells, cytolytic T cells, CD8+ T cells or CTLs) kill cells such as diseased cells.

The term "humoral immune response" refers to a process in living organisms wherein antibodies are produced in response to agents and organisms, which they ultimately neutralize and/or eliminate. The specificity of the antibody response is mediated by T and/or B cells through membrane-associated receptors that bind antigen of a single specificity. Following binding of an appropriate antigen and receipt of various other activating signals, B lymphocytes divide, which produces memory B cells as well as antibody secreting plasma cell clones, each producing antibodies that recognize the identical antigenic epitope as was recognized by its antigen receptor. Memory B lymphocytes remain dormant until they are subsequently activated by their specific antigen. These lymphocytes provide the cellular basis of memory and the resulting escalation in antibody response when re-exposed to a specific antigen.

The term "antibody" as used herein, refers to an immunoglobulin molecule, which is able to specifically bind to an epitope on an antigen. In particular, the term "antibody" refers to a glycoprotein comprising at least two heavy (H) chains and two light (L) chains inter-connected by disulfide bonds. Each heavy chain is comprised of a heavy chain variable region (Vi) and a heavy chain constant region (CH). Each light chain is comprised of a light chain variable region (VL) and a light chain constant region (CL). The variable regions and constant regions are also referred to herein as variable domains and constant domains, respectively. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The CDRs of a VH are termed HCDR1, HCDR2 and HCDR3, the CDRs of a VL are termed LCDR1, LCDR2 and LCDR3. The variable regions of the heavy and light chains contain a binding domain that interacts with an antigen. The constant regions of an antibody comprise the heavy chain constant region (CH) and the light chain constant region (CL), wherein Ci can be further subdivided into constant domain CH1, a hinge region, and constant domains CH2 and CH3 (arranged from amino-terminus to carboxy-terminus in the following order: CH1, CH2, CH3). The constant regions of the antibodies may mediate the binding of the immunoglobulin to host tissues or factors, including various cells of the immune system (e.g., effector cells) and the first component (Clq) of the classical complement system.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e., IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the VL (variable light chain) domain, CL (constant light chain) domain, VH (variable heavy chain) domain, and the CH (constant heavy chain) domains CH1, CH2, CH3, and CH4. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

According to the invention, the term "antigen" or "immunogen" covers any substance, preferably a peptide or protein, that is a target of an immune response and/or that will elicit an immune response. In particular, an "antigen" relates to any substance that reacts specifically with antibodies or T lymphocytes (T cells). According to the present invention, the term "antigen" comprises any molecule which comprises at least one epitope such as a B cell or T cell epitope. Preferably, an antigen in the context of the present invention is a molecule which, optionally after processing, induces an immune reaction, which is preferably specific for the antigen or cells expressing the antigen. According to the present invention, any suitable antigen may be used, which is a candidate for an immune reaction, wherein the immune reaction is preferably a cellular immune reaction. In the context of the embodiments of the present invention, the antigen is preferably presented by a cell, preferably by an antigen presenting cell, in the context of MHC molecules, which results in an immune reaction against the antigen. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof. In preferred embodiments, the antigen is a surface polypeptide, i.e., a polypeptide naturally displayed on the surface of a cell, a pathogen, a bacterium, a virus, a fungus, a parasite, an allergen, or a tumor. The antigen may elicit an immune response against a cell, a pathogen, a bacterium, a virus, a fungus, a parasite, an allergen, or a tumor.

According to the invention, the term "neo-antigen" relates to a peptide or protein including one or more amino acid modifications compared to the parental peptide or protein. For example, the neo-antigen may be a tumor-associated neo-antigen, wherein the term "tumor-associated neo-antigen" includes a peptide or protein including amino acid modifications due to tumor specific mutations.

According to the invention, the term "disease specific mutation" relates to a somatic mutation that is present in the nucleic acid of a diseased cell but absent in the nucleic acid of a corresponding normal, i.e., non-diseased, cell.

According to the invention, the term "tumor specific mutation" or "cancer specific mutation" relates to a somatic mutation that is present in the nucleic acid of a tumor or cancer cell but absent in the nucleic acid of a corresponding normal, i.e., non-tumorous or non-cancerous, cell. The terms "tumor specific mutation" and "tumor mutation" and the terms "cancer specific mutation" and "cancer mutation" are used interchangeably herein.

According to the present invention, an antigen may be selected from the group comprising a self-antigen and non-self-antigen such as a bacterial antigen, a virus antigen, a fungus antigen, an allergen or a parasite antigen.

In a preferred embodiment, an antigen is associated with a disease or disorder, i.e., the antigen is a disease-associated antigen. The term "disease-associated antigen" refers to all antigens that are of pathological significance. In one particularly preferred embodiment, a disease-associated antigen is present in diseased cells, tissues and/or organs while it is not present or present in a reduced amount in healthy cells, tissues and/or organs and, thus, can be used for targeting diseased cells, tissues and/or organs. In one embodiment, a disease-associated antigen is present on the surface of a diseased cell. In one embodiment, a disease-associated antigen is a molecule which contains at least one epitope that will stimulate a host's immune system to make a humoral and/or cellular immune response against the disease. The disease-associated antigen may therefore be used for therapeutic purposes. Disease-associated antigens are preferably associated with infection by microbes, typically microbial antigens, or associated with cancer, typically tumors.

In some embodiments the antigen is or is derived from a bacterial antigen. In some embodiments, the antigen elicits an immune response against a bacterium which infects animals, including birds, fish and mammals, including domesticated animals. Preferably, the bacterium against which the immune response is elicited is a pathogenic bacterium.

In some embodiments the antigen is or is derived from a virus antigen. A virus antigen may for example be a peptide from a virus surface protein, e.g. a capsid polypeptide or a spike polypeptide. In some embodiments, the antigen elicits an immune response against a virus which infects animals, including birds, fish and mammals, including domesticated animals. Preferably, the virus against which the immune response is elicited is a pathogenic virus.

In some embodiments the antigen is or is derived from a peptide or protein from a fungus. In some embodiments, the antigen elicits an immune response against a fungus which infects animals, including birds, fish and mammals, including domesticated animals. Preferably, the fungus against which the immune response is elicited is a pathogenic fungus.

In some embodiments the antigen is or is derived from a peptide or protein from a unicellular eukaryotic parasite. In some embodiments, the antigen elicits an immune response against a unicellular eukaryotic parasite, preferably a pathogenic unicellular eukaryotic parasite. Pathogenic unicellular eukaryotic parasites may be e.g. from the genus *Plasmodium*, e.g. *P. falciparum*, *P. vivax*, *P. malariae* or *P. ovale*, from the genus *Leishmania*, or from the genus *Trypanosoma*, e.g. *T. cruzi* or *T. brucei*.

In some embodiments the antigen is or is derived from an allergenic peptide or an allergenic protein. An allergenic peptide or allergenic protein is suitable for allergen immunotherapy, also known as hypo-sensitization.

In a preferred embodiment, an antigen is a tumor antigen or tumor-associated antigen, i.e., a constituent of cancer cells which may be derived from the cytoplasm, the cell surface and the cell nucleus, in particular those antigens which are produced, preferably in large quantity, as surface antigens on cancer cells.

In the context of the present invention, the term "tumor antigen" or "tumor-associated antigen" relates to proteins that are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably associated with the cell surface of a cancer cell and is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor antigen is identical between the tumor antigen which is expressed in normal tissues and the tumor antigen which is expressed in cancer tissues.

Examples for tumor antigens that may be useful in the present invention are p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NFL, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, rEUAML1, TPI/m, TRP-1, TRP-2, TRP-2/INT2, TPTE and WT. Particularly preferred tumor antigens include CLAUDIN-18.2 (CLDN18.2) and CLAUDIN-6 (CLDN6).

An antigen which may be provided according to the invention to a subject either by administering the antigen or a nucleic acid coding for the antigen, i.e., a vaccine antigen, should result in a T cell response. The T cells should be directed against a target antigen, in particular a target antigen expressed by or in diseased cells, tissues and/or organs, i.e., a disease-associated antigen. Thus, a vaccine antigen may correspond to or comprise the disease-associated antigen, or it may be a variant thereof. In one embodiment, such variant is immunologically equivalent to the disease-associated antigen. In the context of the present invention, the term "variant of an antigen" means an agent which results in a T cell response targeting the antigen, i.e., a disease-associated antigen, in particular when expressed in diseased cells, tissues and/or organs, or cells expressing the antigen and optionally presenting the antigen in the context of MHC molecules. Thus, the vaccine antigen may be identical to the disease-associated antigen, may comprise the disease-associated antigen or a portion thereof or may comprise an antigen which is homologous to the disease-associated antigen or a portion thereof. If the vaccine antigen comprises a portion of the disease-associated antigen or a portion of an antigen which is homologous to the disease-associated antigen said portion may comprise an epitope of the disease-associated antigen to which the T cell response is to be targeted. Thus, according to the invention, an antigen may comprise an immunogenic fragment of a disease-associated antigen such as a peptide fragment of a disease-associated antigen. An "immunogenic fragment of an antigen" according to the invention preferably relates to a portion or fragment of an antigen which is capable of stimulating a T cell response. The vaccine antigen or the nucleic acid encoding a vaccine antigen to be administered according to the invention may be a recombinant antigen or recombinant nucleic acid.

The term "epitope" refers to an antigenic determinant in a molecule such as an antigen, i.e., to a part in or fragment of the molecule that is recognized, i.e., bound, by the immune system, for example, that is recognized by an antibody or T cell receptor. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. Preferably an epitope is capable of eliciting an immune response against the antigen or a cell expressing the antigen. Preferably, the term relates to an immunogenic portion of an antigen comprising the epitope. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is preferred that the epitope in the context of the present invention is a T cell epitope.

As used herein, the term "T cell epitope" refers to a peptide which binds to a MHC molecule in a configuration recognized by a T cell receptor. Typically, T cell epitopes are presented on the surface of an antigen presenting cell. A "T cell epitope" according to the invention preferably relates to a portion or fragment of an antigen which is capable of stimulating an immune response, preferably a cellular response against the antigen or cells characterized by expression of the antigen and preferably by presentation of the antigen. Preferably, a T cell epitope is capable of stimulating a cellular response against a cell characterized by presentation of an antigen. Preferably, T cell epitopes are MHC class I and/or class II presented peptides. Preferably, T cell epitopes comprise an amino acid sequence substantially corresponding to the amino acid sequence of a fragment of an antigen. Preferably, said fragment of an antigen is an MHC class I and/or class II presented peptide. A peptide which is suitable for binding to an MHC molecule, in particular a class I MHC molecule, preferably is 7-20 amino acids in length, more preferably 7-12 amino acids in length, more preferably 8-11 amino acids in length, in particular 9 or 10 amino acids in length. In one embodiment, a T cell epitope when presented in the context of MHC such as MHC of antigen presenting cells is recognized by a T cell receptor. The T cell epitope if recognized by a T cell receptor may be able to induce in the presence of appropriate co-stimulatory signals, clonal expansion of the T cell carrying the T cell receptor specifically recognizing the T cell epitope. Preferably, T cell epitopes, in particular if presented in the context of MHC molecules, are capable of stimulating an immune response, preferably a cellular response against the antigen from which they are derived or cells characterized by expression of the antigen and preferably characterized by presentation of the antigen.

According to the invention, a T cell epitope may be present in a vaccine antigen as a part of a larger entity such as a vaccine sequence and/or a polypeptide comprising more than one T cell epitope. The presented peptide or T cell epitope is produced following suitable processing. Also, T cell epitopes may be modified at one or more residues that are not essential for TCR recognition or for binding to MHC. Such modified T cell epitopes may be considered immunologically equivalent.

Vaccination according to the invention using antigens as described herein preferably results in an immune response against disease-associated antigens or epitopes thereof. Preferably, such disease-associated antigens or epitopes thereof comprise one or more disease specific amino acid modifications, e.g. they comprise or are disease-associated neo-antigens or neo-epitopes. Preferably, a disease specific amino acid modification is due to one or more disease specific somatic mutations. In one particularly preferred embodiment, a disease specific amino acid modification is a cancer specific amino acid modification and a disease specific somatic mutation is a cancer specific somatic mutation. Thus, in one embodiment, a vaccine antigen preferably features disease specific amino acid modifications/disease specific somatic mutations of a patient and preferably upon administration provides one or more mutation based neo-epitopes. Thus, the vaccine antigen may comprise a peptide or polypeptide comprising one or more mutation based neo-epitopes. In one embodiment, disease specific amino acid modifications are identified by identifying disease specific somatic mutations, e.g. by sequencing genomic DNA and/or RNA of diseased tissue such as cancer tissue or one or more diseased cells such as cancer cells.

As used herein the term "neo-epitope" refers to an epitope that is not present in a reference such as a normal non-diseased (e.g. non-cancerous) or germline cell but is found in diseased cells (e.g. cancer cells). This includes, in particular, situations wherein in a normal non-diseased or germline cell a corresponding epitope is found, however, due to one or more mutations in a diseased cell the sequence of the epitope is changed so as to result in the neo-epitope.

According to the invention, the term "vaccine" relates to a pharmaceutical preparation (pharmaceutical composition) or product that upon administration induces an immune response, which recognizes and attacks a pathogen or a diseased cell such as a cancer cell. A vaccine may be used for the prevention or treatment of a disease. In particular, the term "vaccine" refers to a composition that includes an antigen, as defined herein.

In one embodiment, a vaccine provided according to the invention comprises a vaccine antigen, herein also referred to simply as "antigen", as described herein for stimulating a therapeutically or prophylactically useful immune response or a nucleic acid, preferably RNA, encoding peptide or protein antigen.

The antigens described herein when administered to a subject preferably provide one or more epitopes suitable for stimulating a disease-specific immune response. In one embodiment, the disease-specific immune response is an antigen-specific immune response which preferably is directed against a disease-associated antigen or cells expressing a disease-associated antigen and presenting the disease-associated antigen in the context of MHC molecules. Presentation of these epitopes, e.g. by diseased cells or pathogenic agents, serves as a label for targeting by the immune response.

The immunotherapeutic approaches according to the invention include immunization with peptide or protein antigen (native or modified), nucleic acid encoding peptide or protein antigen, recombinant cells encoding peptide or protein antigen, recombinant viruses encoding peptide or protein antigen and antigen presenting cells pulsed with peptide or protein antigen (native or modified) or transfected with nucleic acids encoding peptide or protein antigen.

In one embodiment of the invention, a nucleic acid such as RNA that codes for an antigen is administered to a subject. An antigenic translation product of the nucleic acid may be formed in cells of the subject and the product may be displayed to the immune system for stimulation of an immune response.

Alternatively, the present invention envisions embodiments wherein a nucleic acid expressing an antigen recited herein is introduced into cells such as antigen-presenting cells ex vivo, e.g. antigen-presenting cells taken from a patient, and the cells, optionally clonally propagated ex vivo, are transplanted back into the same patient. Transfected cells may be reintroduced into the patient using any means known in the art, preferably in sterile form by intravenous, intracavitary, intraperitoneal or intratumor administration.

The immunotherapeutic approaches according to the invention also include transfer of T cell receptors that recognize protein or peptide, and effector cells (such as T cells) encoding receptors that recognize peptide or protein antigen, in particular when presented in the context of MHC, also termed "antigen receptor" herein.

Preferred proteins and fragments according to the invention are antigens expressed in a disease specific manner, e.g. they are disease-associated antigens or epitopes, (e.g., the presence of a protein or cells expressing a protein is characteristic for the disease) and/or comprise one or more disease specific amino acid modifications, e.g., they are disease-associated neo-antigens or neo-epitopes.

In one embodiment, the aim is to provide an immune response against cancer cells expressing a tumor antigen and to treat a cancer disease involving cells expressing a tumor antigen. Said cancer cells expressing a tumor antigen may present the tumor antigen on the cell surface in the context of MHC molecules. Cancer cells presenting a tumor antigen on the cell surface in the context of MHC molecules can be targeted by T cells directed to a T cell epitope of the tumor antigen.

"Cell surface" is used in accordance with its normal meaning in the art, and thus includes the outside of the cell which is accessible to binding by proteins and other molecules. An antigen is expressed on the surface of cells if it is located at the surface of said cells and is accessible to binding by e.g. antigen-specific antibodies added to the cells.

The terms "portion" or "part" are used interchangeably herein and refer to a continuous or discontinuous element of a structure such as an amino acid or nucleic acid sequence. The term "fragment" refers to a continuous element of a structure such as an amino acid sequence. A portion, part or fragment of a structure preferably comprises one or more functional properties, e.g. antigenic, immunologic and/or binding properties, of said structure. A portion or part of a protein sequence preferably comprises at least 6, in particular at least 8, at least 12, at least 15, at least 20, at least 30, at least 50, or at least 100 consecutive and/or non-consecutive amino acids of the protein sequence. A fragment of a protein sequence preferably comprises at least 6, in particular at least 8, at least 12, at least 15, at least 20, at least 30, at least 50, or at least 100 consecutive amino acids of the protein sequence.

The term "immunogenicity" relates to the relative effectivity of an antigen to induce an immune reaction.

As used herein, the term "immunogenic" relates to the property of having immunogenicity.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "target" shall mean an agent such as a cell, in particular a cancer cell, which is a target for an immune response. Targets include cells that present an antigen or an antigen epitope, i.e., a peptide fragment derived from an antigen. In one embodiment, the target cell is a cell expressing a target antigen which is preferably presented with class I MHC.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that displays antigen in the context of major histocompatibility complex (MHC) on its surface. T cells may recognize this complex using their T cell receptor (TCR). Antigen-presenting cells process antigens and present them to T cells. An antigen presenting cell includes, but is not limited to, monocytes/macrophages, B cells and dendritic cells (DCs). According to the invention, the term "antigen-presenting cell" includes professional antigen-presenting cells and non-professional antigen-presenting cells.

Professional antigen-presenting cells are very efficient at internalizing antigen, either by phagocytosis or by receptor-mediated endocytosis, and then displaying a fragment of the antigen, bound to a MHC class II molecule, on their membrane. The T cell recognizes and interacts with the antigen-MHC class II molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Non-professional antigen-presenting cells do not constitutively express the MH C class II proteins required for interaction with naive T cells; these are expressed upon stimulation of the non-professional antigen-presenting cells by certain cytokines such as IFNγ.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of immunity.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

By "cell characterized by presentation of an antigen" or "cell presenting an antigen" or similar expressions is meant a cell such as a diseased cell, e.g. a cancer cell, or an antigen presenting cell presenting an antigen or a fragment derived from said antigen, e.g. by processing of the antigen, in the context of MHC molecules, in particular MHC class 1 molecules. Similarly, the terms "disease characterized by presentation of an antigen" denotes a disease involving cells characterized by presentation of an antigen, in particular with MHC class 1.

The term "immunoreactive cell" or "effector cell" in the context of the present invention relates to a cell which exerts effector functions during an immune reaction. An "immunoreactive cell" preferably is capable of binding an antigen or a cell characterized by expression and/or presentation of an antigen or an epitope and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells.

The term "immune effector functions" or "effector functions" in the context of the present invention includes any functions mediated by components of the immune system that result, for example, in the killing of cells. Preferably, the immune effector functions in the context of the present invention are T cell mediated effector functions. Such functions comprise in the case of a helper T cell (CD4+ T cell) the recognition of an antigen or an antigen peptide derived from an antigen in the context of MHC class II molecules by T cell receptors, the release of cytokines and/or the activation of CD8+ lymphocytes (CTLs) and/or B-cells, and in the case of CTL the recognition of an antigen or an antigen peptide derived from an antigen in the context of MHC class I molecules by T cell receptors, the elimination of cells presented in the context of MHC class I molecules, i.e., cells characterized by presentation of an antigen with MHC class I, for example, via apoptosis or perforin-mediated cell lysis, production of cytokines such as IFN-γ and TNF-α, and specific cytolytic killing of antigen expressing target cells.

Preferably, an "immunoreactive cell" recognizes an antigen or an epitope with some degree of specificity, in particular if presented in the context of MHC molecules such as on the surface of antigen presenting cells or diseased cells such as tumor cells. Preferably, said recognition enables the cell that recognizes an antigen or an epitope to be responsive or reactive. If the cell is a helper T cell (CD4+ T cell) bearing receptors that recognize an antigen or an epitope in the context of MHC class II molecules such responsiveness or reactivity may involve the release of cytokines and/or the activation of CD8+ lymphocytes (CTLs) and/or B-cells. If the cell is a CTL such responsiveness or reactivity may involve the elimination of cells presented in the context of MHC class I molecules, i.e., cells characterized by presentation of an antigen with MHC class I, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognize an antigen or an epitope and are responsive or reactive are also termed "antigen-responsive CTL" herein. If the cell is a B cell such responsiveness may involve the release of immunoglobulins.

The term "T cell" or "T lymphocyte" relates to thymus-derived cells that participate in a variety of cell-mediated immune reactions and includes T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and ρ-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The structure of the T cell receptor is very similar to immunoglobulin Fab fragments, which are regions defined as the combined light and heavy chain of an antibody arm. Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end. The variable domain of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens. The constant domain of the TCR domain consists of short connecting sequences in which a cysteine residue forms disulfide bonds, which forms a link between the two chains.

According to the invention the term "antigen receptor" includes naturally occurring receptors such as T cell receptors as well as engineered receptors, which confer an arbitrary specificity such as the specificity of a monoclonal antibody onto an effector cell such as a T cell. In this way, a large number of antigen-specific T cells can be generated for adoptive cell transfer. Thus, an antigen receptor according to the invention may be present on T cells, e.g. instead of or in addition to the T cell's own T cell receptor. Preferably, said antigen receptor is expressed on the surface of the cells. For the purpose of the present invention T cells comprising engineered antigen receptor are comprised by the term "T cell" as used herein. Specifically, according to the invention, the term "antigen receptor" includes artificial receptors comprising a single molecule or a complex of molecules which recognize, i.e., bind to, a target structure (e.g. a MHC peptide complex) on a target cell such as a cancer cell and may confer specificity onto an effector cell such as a T cell expressing said antigen receptor on the cell surface. Preferably, recognition of the target structure by an antigen receptor results in activation of an effector cell expressing said antigen receptor. According to the invention an "antigen receptor" may be a "chimeric antigen receptor (CAR)", "chimeric T cell receptor" or "artificial T cell receptor".

The term "B cell" or "B lymphocyte" relates to a type of white blood cell of the lymphocyte subtype which function in humoral immunity by secreting antibodies. Additionally, B cells present antigens and are classified as professional antigen-presenting cells (APCs) and secrete cytokines. B cells express B cell receptors (BCRs) on their cell membrane. BCRs allow the B cell to bind a specific antigen, against which it will initiate an antibody response. The B-cell receptor is composed of two parts, a membrane-bound immunoglobulin molecule of one isotype (IgD, IgM, IgA, IgG, or IgE) which with the exception of the presence of an integral membrane domain are identical to their secreted forms and a signal transduction moiety; a heterodimer called Ig-α/Ig-β (CD79), bound together by disulfide bridges. Each member of the dimer spans the plasma membrane and has a cytoplasmic tail bearing an immunoreceptor tyrosine-based activation motif (TAM).

B cell activation occurs in the secondary lymphoid organs, such as the spleen and lymph nodes. After B cells mature in the bone marrow, they migrate through the blood to secondary lymphoid organs, which receive a constant supply of antigen through circulating lymph. B cell activation begins when the B cell binds to an antigen via its BCR.. Different B cell subsets undergo T cell-dependent activation or T cell-independent activation.

The term "peripheral blood mononuclear cell" or "PBMC" relates to a peripheral blood cell having a round nucleus. These cells consist of lymphocytes (T cells, B cells, NK cells) and monocytes, whereas erythrocytes and platelets have no nuclei, and granulocytes (neutrophils, basophils, and eosinophils) have multi-lobed nuclei. These cells can be extracted from whole blood using ficoll and gradient centrifugation, which will separate the blood into a top layer of plasma, followed by a layer of PBMCs and a bottom fraction of polymorphonuclear cells (such as neutrophils and eosinophils) and erythrocytes.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self-antigens (peptide fragments from the cell itself) and non-self-antigens (e.g., fragments of invading microorganisms) to a T cell.

The MHC region is divided into three subgroups, class I, class II, and class III. MHC class I proteins contain an α-chain and δ2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPA1, HLA-DPB1, HLA-DQA1, HLA-DQB1, HILA-DRA, and HLA-DRB1.

In one preferred embodiment of all aspects of the invention an MHC molecule is an HLA molecule.

MHC class I molecules are one of two primary classes of major histocompatibility complex (MHC) molecules and are found on the cell surface of all nucleated cells in the bodies of jawed vertebrates. They also occur on platelets, but not on red blood cells. Their function is to display peptide fragments of non-self-proteins generated mainly from degradation of cytosolic proteins by the proteasome to cytotoxic T cells; this will trigger an immediate response from the immune system against a particular non-self-antigen displayed with the help of an MHC class I protein. Because MHC class I molecules present peptides derived from cytosolic proteins, the pathway of MHC class I presentation is often called cytosolic or endogenous pathway. Thus, the function of the MHC class I is to display intracellular proteins to cytotoxic T cells (CTLs). However, MHC class I can also present peptides generated from exogenous proteins, in a process known as cross-presentation. In humans, the HLAs corresponding to MHC class I are HLA-A, HLA-B, and HL A-C.

MHC class I molecules are heterodimers that consist of two polypeptide chains, the α chain and β2-microglobulin (B2M). The two chains are linked non-covalently via interaction of B2M and the α3 domain. Only the α chain is polymorphic and encoded by a HLA gene, while the B2M subunit is not polymorphic. In humans, the β2-microglobulin protein is encoded by the B2M gene. The α3 domain is plasma membrane-spanning and interacts with the CD8 co-receptor of T cells. The α3-CD8 interaction holds the MHC I molecule in place while the T cell receptor (TCR) on the surface of the cytotoxic T cell binds its α1-α2 heterodimer ligand, and checks the coupled peptide for antigenicity. The α1 and α2 domains fold to make up a groove for peptides to bind. MHC class I molecules bind peptides that are 8-10 amino acids in length.

Mouse models deficient for the β2-microglobulin gene have been engineered. These mice demonstrate that β2-microglobulin is necessary for cell surface expression of MHC class I and stability of the peptide binding groove. In fact, in the absence of β2-microglobulin, very limited amounts of MHC class I (classical and non-classical) molecules can be detected on the surface.

The present invention identifies a chromosomal deletion and inversion event in chromosome 15 resulting in B2M deletion. The chromosomal deletion and inversion event in chromosome 15 resulting in B12M deletion identified according to the invention preferably is after (i.e., downstream of) position chr15:44,962,085. The chromosomal deletion and inversion event in chromosome 15 resulting in 1B2M deletion identified according to the invention preferably involves the following sequence on chromosome 15 or the complementary sequence, wherein ♦ indicates the breakpoints of the chromosomal deletion and inversion event and n is an integer from 0 to 5, preferably 0 or 1:

```
[...(chr15:45,166,884-45,304,326
(137,444 bp))SEQ ID NO: 6)]
CCCTAAGGAACTGATATCTCACCTTCTCAATCCGGTATAATACCCGAA

GCCTCTGACTGCTTGCAGCTTCTATATCCTAGGAGAAGGGAGTCACCA

GCTATCAGCTACACTGCCACTGCCACAGCCCTAGCCCAGGCCCCCAAC

TAGCTAGAGATTGAGCTGGAAAGGCTAGAAACAAAGTCTGATCACACT

TCTTCCTCCTTCTTCGGTCACAGTCTTAAACACAAGAATGTTCTAGAC

CCTTCTTCCAAAGGGGAGAGAAAAATGTCTGGGAAGATAGTGCTCCCA

CCTGCTCTTGAGTTCCATGGGGTACCGCATCAATAGCTCGGCGAGGGC

TGAAGCATGTCGACACAGCTACCTGGCCCAGGGAACCCTCGATTCGGA

CCACTGCATGAGAAGA♦(A)nAACCTATAGCGGGTTTTTTGTGGTCCC

TTGGAGATTTCTTTGCTTGTTTCCTTCTGGGTGGGGAGATTAGAGGA

GGCTCATCATTAATAGGAAGGAAGAGGAGCTGTAAGGAGGCTAGGATA

TGGGGGTAAGCTGAGAGGTCCTCCTGTGGAATGTAGATTGCAAGCTTT

GCATAGTTGTGGATTGTCCTTCAGTGAAAAGAAAGCTTGGACATAAGG
```

-continued
TATTTCACTCCACTTGCCTTCCTTCTTACAGAAAAGTTCAAGCTGCAG

GATACTATTGTAATTTATACGTCCCTCAGGTGG (SEQ ID NO: 5)
CTCACACTTGAAATGCATCCTAAGCCATTGGGATGAATTTGACCTGCA

AGCCCTGAAAAGAAGAGGCTTATTTTTTTCTGCACTGTGGCCTGGTC

CCAATATTCTCTCTCTGATAGGGAAAAATGGCCACCTGTGGAAAGTAT

AAATTACAGTATTATCCTGCAGCTTGACTTTTTCTGTAAGATGGAAGG

CAAATGGAGTGAAATACCTTATGTCCAAGCTTTCTTTTCACTGAAGGA

CAATCCACAACTATGCAAAGCTTGCAACCTACATTCCACAGGAGGACC

TCTCAGCTTACCCC♦ATGTCCTCTTCAAGCTGTAGGGGAGGGGAAT

TTGGCCCAACCCGGGTACAAGTCCCCTTCTCCCTCTCTGATTTAAAGC

AGATCAAGTTAGATCTGGGGAAGTTTTCAGGTGATCCTGATAGGTATA

TAGATATCCTATGGGGTCTAGGGCAAACCTTCGACCTCACTTGGAGAG

ATGTCATGCTATTGTTTTGTTGCTGTTGTTGTTTTGAGATGGAGT

TTCACTCTGTTGCCCAGGCTGGAGTGCAGTGGCACAATCTCAGCTCAC

TGCAAGCTCCACTTCCCGGGTTCACACCA

The sequence surrounding the end point of the deletion, which is the start point of the inverted region preferably comprises the sequence AGGTT(T)nTCTTC (SEQ ID NO: 9), preferably GCTATAGGTT(T)nTCTTCTCATG (SEQ ID NO: 11) such as CAAAAAACCCGCrATAGGTT(T)nTC-TrCrCATGCAGrGGTCCG (SEQ ID NO: 13), wherein n is an integer from 0 to 5, preferably 0 or 1, or the complementary sequence.

According to the invention, a sequence comprising the sequence AGGTr(T)nTCTTC (SEQ ID NO: 9) comprises a sequence comprising the sequence GCTATAGGTT(T)nTCTTCTCATG (SEQ ID NO: 11) and a sequence comprising the sequence CAAAAAACCCGCTATAGGTT(T)nTCTTCTCATGCAGTGGCCG (SEQ ID NO: 13), wherein n is an integer from 0 to 5, preferably 0 or 1.

According to the invention, a sequence comprising the sequence AGGTTTTCTTC (SEQ ID NO: 10) comprises a sequence comprising the sequence GCTATAGGTTTTCTTCTCATG (SEQ ID NO: 12) and a sequence comprising the sequence CAAAAAACCCGC-TATAGGTTTTCTTCTCATGCAGTGGTCCG (SEQ ID NO: 14).

In one embodiment, the sequence surrounding the end point of the deletion, which is the start point of the inverted region comprises the sequence:

(SEQ ID NO: 17)
CCACCCAGAAGGAAACAAGCAAAGAAATCTCCAAGGGACCACAAAAAA

CCCGCTATAGGTTTCTTCTCATGCAGTGGTCCGAATCGAGGGTTC.

In one embodiment, the sequence surrounding the end point of the deletion, which is the start point of the inverted region comprises the sequence:

(SEQ ID NO: 21)
CAAGCAAAGAAATCTCCAAGGGACCACAAAAAACCCGCTATAGGTTTT

CTTCTCATGCAGTGGTCCGAATCGAGGGTTCCCTGGGCCA.

The chromosomal deletion and inversion event in chromosome 15 resulting in B2M deletion identified according to the invention preferably is characterized by a sequence surrounding the end point of the deletion, which is the start point of the inverted region as described herein.

Identifying a chromosomal deletion and inversion event in a chromosome 15 according to the invention preferably comprises performing a nucleic acid amplification reaction such as PCR with genomic DNA using primers wherein one of the primers hybridizes in a region upstream to the deleted region and the other primer hybridizes within the inverted sequence. Thus, the amplification product preferably comprises the sequence surrounding the end point of the deletion, which is the start point of the inverted region such as a sequence surrounding the end point of the deletion, which is the start point of the inverted region as described herein. In one embodiment, the amplification product preferably comprises the sequence surrounding position chr15:44,962,085, and preferably comprises 5 or more, 10 or more, 20 or more, 30 or more, 40 or more and preferably up to 80, 60, or 50 nucleotides on each side of said position.

Primer pairs useful according to the invention for performing a nucleic acid amplification reaction such as PCR to identify a chromosomal deletion and inversion event in a chromosome are as follows:

(SEQ ID NO: 15)
5' AGCATGTCGACACAGCTACC 3',
and (SEQ ID NO: 16)
5' ACCTCTCAGCTTACCCCCAT 3';

(SEQ ID NO: 18)
5' GAACCCTCGATTCGGACCAC 3',
and (SEQ ID NO: 19)
5' CCACCCAGAAGGAAACAAGC 3';

(SEQ ID NO: 22)
5' CAAGCAAAGAAATCTCCAAGGGA 3',
and (SEQ ID NO: 23)
5' TGGCCCAGGGAACCCTC 3'.

The term "genotype" refers to the genetic makeup of an organism, i.e., it describes an organism's complete set of genes. In a more narrow sense, the term can be used to refer to the alleles, or variant forms of a gene, that are carried by an organism. Humans are diploid organisms, which means that they have two alleles at each genetic position, or locus, with one allele inherited from each parent. Each pair of alleles represents the genotype of a specific gene. A particular genotype is described as homozygous if it features two identical alleles and as heterozygous if the two alleles differ. The process of determining a genotype is called genotyping.

The term "allele" is used herein to refer to a variant of a nucleotide sequence.

The term "deletion" refers to a mutation (a genetic aberration) in which a part of a chromosome or a sequence of DNA is lost. Any number of nucleotides can be deleted, from a single base to an entire piece of chromosome.

The term "inversion" refers to a chromosome rearrangement in which a segment of the chromosome breaks off and is reinserted in the same place but in the reverse direction relative to the rest of the chromosome.

According to the invention, the presence of a chromosomal deletion and inversion event in a subject may be detected using any technique known in the art. Generally, a nucleic acid sample from the subject will be provided and analyzed to detect the presence or absence of at least one copy of a chromosomal deletion and inversion event, to detect the presence of exactly one copy of a chromosomal deletion and inversion event, or to detect the presence of exactly two copies of a chromosomal deletion and inversion event. In some embodiments the method comprises analyzing the nuclear DNA of the subject.

The term "sample containing nucleic acid" or "nucleic acid sample" includes a sample from a subject to be tested according to the invention. If genomic DNA in the sample will be analyzed the sample can come from any tissue source that comprises genomic DNA of the subject, including, without limitation, blood, blood-derived product (such as buffy coat, serum, and plasma), lymph, urine, tear, saliva, hair bulb cells, cerebrospinal fluid, buccal swabs, feces, synovial fluid, synovial cells, sputum, or tissue samples such as cancer tissue samples. In addition, one of skill in the art would realize that some samples would be more readily analyzed following a fractionation or purification procedure, for example, isolation of DNA from whole blood.

In some embodiments, the sample is collected from the subject and then tested with little or no sample processing. In some embodiments the sample is processed, such as for example and without limitation processing to isolate all or a portion of the nucleic acid in the sample, such as genomic DNA in the sample. DNA for detection can be prepared from a biological sample by methods well known in the art, e.g., using commercially available DNA isolation kits.

Numerous methods and devices are well known to the skilled artisan to identify the presence or absence of a chromosomal deletion and inversion event. Any method known in the art or later developed may be used, in view of the teachings of this disclosure, to detect a chromosomal deletion and inversion event in a sample comprising genomic DNA obtained from a subject.

In general, methods for detecting a chromosomal deletion and inversion event can be divided into two groups: (1) methods based on hybridization analysis of polynucleotides, and (2) other methods based on biochemical detection or sequencing of polynucleotides. The method used may be based on analysis of a starting nucleic acid that is genomic DNA obtained from the subject.

Detection of a chromosomal deletion and inversion event may include examining the nucleotide(s) located at either the sense or the anti-sense strand within the region of the chromosomal deletion and inversion event. For the detection of a chromosomal deletion and inversion event, sequence specific primers and/or probes may be designed such that they specifically hybridize to the genomic DNA for the allele of interest and/or amplify a DNA segment of a size and/or sequence characteristic of the chromosomal deletion and inversion event. Probes or primers may be labeled for direct detection. PCR products also can be detected by DNA-binding agents. PCR products can also be sequenced by any DNA sequencing method available in the art. Alternatively, the presence or absence of an allele can be detected by sequencing using any sequencing methods such as, but not limited to, Sanger-based sequencing, pyrosequencing or next generation sequencing.

In one particularly preferred embodiment, detecting a chromosomal deletion and inversion event comprises performing polymerase chain reaction (PCR), in particular quantitative real-time PCR (qRT-PCR).

The term "polymerase chain reaction" or "PCR" relates to the amplification of a target sequence of DNA which proceeds through a series of temperature regulated cycles using the activity of a thermostable enzyme and a sequence specific primer set. At an appropriate temperature, the primers hybridize to portions of the target DNA strand and the enzyme successively adds a plurality of nucleotide bases to elongate the primer which results in the production of progeny (daughter) strands. Each progeny strand possesses a complementary composition relative to the target template strand from which it was derived, and can serve as a template in subsequent reaction cycles.

According to the invention, primer pairs may be selected for amplification which are specific for a chromosomal deletion and inversion event described herein and/or result in an amplification product which is specific for a chromosomal deletion and inversion event described herein, e.g., they may result in an amplification product of a size which is characteristic for the presence of the chromosomal deletion and inversion event.

According to the invention it is also possible to apply quantitative methods to PCR-based technologies. In one embodiment, a PCR-based method known as quantitative real-time PCR (qRT-PCR or qPCR) may be used according to the invention to identify and, optionally, quantify target nucleotide strands or fragments in a sample population. For example, a fluorescent probe or other detectable reporter may be incorporated into the reaction to provide a means for determining the progress of the template amplification. Thus, in one embodiment, the present invention integrates the use of a detectable reporter, or probe, which can comprise, for instance, both a fluorescent label molecule and a quencher molecule. Ordinarily, the quencher nullifies the majority of fluorescence which may be emitted by the reporter. During the amplification process, however, both molecules may be released from the probe allowing the fluorescent label to be detected. The quantity or intensity of fluorescence may then be correlated with the amount of product formed in the reaction. In the case of a fluorescent probe, the reaction fluoresces in relative proportion to the quantity of DNA product produced. For instance, the TaqMan® procedure describes one such fluorescent methodology for performing Quantitative PCR. Another reporter according to the invention is SYBR® Green, a DNA-binding dye. Reporting mechanisms using the principle of hybridization (LightCycler® probe) based detection may also be used. LightCycler® technology uses two fluorescent oligonucleotide probes one labeled at the 3' and the other at the 5' end with a phosphorylation modification at the 3 end to prevent extension. Following target amplification, LightCycler® primers hybridize to the target in a head-to-tail configuration, bringing the fluorophores into close proximity. Excitation of the donor fluorophore by an LED light source results in a FRET-based increase in fluorescence emitted by the energy-accepting reporter fluorophore. Although both TaqMan and LightCycler implement a double-label system and have been reported to be of similar accuracy and performance, LightCycler® hybridization probes do not require the probe hydrolysis necessary for fluorescence emission and detection with TaqMan.

For purposes of the invention, the term "real-time PCR" applies to any technique which allows relative monitoring of the evolution of an ongoing polymerase chain reaction amplification.

Another object of the invention is to provide a kit suitable for carrying out methods of the invention as defined herein, especially for use in a genotyping assay according to the present disclosure, comprising:

at least one pair of oligonucleotide primers specific for hybridization with a target sequence in human genomic DNA, preferably a pair of oligonucleotide primers as described herein, and, optionally, one or several of the following reagents:

nucleotides (e.g. dATP, dCTP, dGTP, dTTP), a DNA polymerase, in particular a thermostable DNA polymerase, optionally, at least one probe or other detectable reporter for determining the progress of the template amplification, e.g., a probe or reporter as described herein, optionally, a buffer solution, optionally, reagents necessary for the hybridization of the primers to their targets, optionally, a positive control, optionally, a negative control, optionally, a reference dye and, optionally, a notice providing instructions for use and expected values for interpretation of results.

In some embodiments, the presence or absence of a chromosomal deletion and inversion event in a patient is detected using a hybridization assay. In a hybridization assay, the presence or absence of the genetic marker is determined based on the ability of the nucleic acid from the sample to hybridize to a complementary nucleic acid molecule, e.g., an oligonucleotide probe. A variety of hybridization assays are available. In some, hybridization of a probe to the sequence of interest is detected directly by visualizing a bound probe, e.g., a Southern assay. In these assays, DNA is isolated. The DNA is then cleaved with a series of restriction enzymes that cleave infrequently in the genome and not near any of the markers being assayed. The DNA is then separated, e.g., on an agarose gel, and transferred to a membrane. A labeled probe is allowed to contact the membrane under low-, medium- or high-stringency conditions. Unbound probe is removed and the presence of binding is detected by visualizing the labeled probe.

Amplification primers or simply primers are defined as being a pair of nucleic acid molecules that can anneal to 5' or 3' regions of a nucleic acid region (plus and minus strands, respectively, or vice-versa) and contain a short region in between. In general, amplification primers are from about 10 to about 30 nucleotides in length and flank a region from about 50 to about 200 nucleotides in length. Under appropriate conditions and with appropriate reagents, such primers permit the amplification of a nucleic acid molecule comprising the nucleotide sequence flanked by the primers. PCR products can be detected by any suitable method including, but not limited to, gel electrophoresis and staining with a DNA-specific stain or hybridization to a labeled probe. Thus, the term "primer" denotes a specific oligonucleotide sequence which is complementary to a target nucleotide sequence and used to hybridize to the target nucleotide sequence. A primer serves as an initiation point for nucleotide polymerization catalyzed, for example, by DNA polymerase.

The term "probe" denotes a defined nucleic acid segment which can be used to identify a specific polynucleotide sequence present in samples, said nucleic acid segment comprising a nucleotide sequence complementary of the specific polynucleotide sequence to be identified.

Any suitable sequencing method can be used according to the invention, Next Generation Sequencing (NGS) technologies being preferred. Third Generation Sequencing methods might substitute for the NGS technology in the future to speed up the sequencing step of the method. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention e.g. those described in detail in Zhang et al. 2011: The impact of next-generation sequencing on genomics. J. Genet Genomics 38 (3), 95-109; or in Voelkerding et al. 2009: Next generation sequencing: From basic research to diagnostics. Clinical chemistry 55, 641-658. Non-limiting examples of such NGS technologies/platforms are 1) The sequencing-by-synthesis technology known as pyrosequencing implemented e.g. in the GS-FLX 454 Genome Sequencer™ of Roche-associated company 454 Life Sciences (Branford, Connecticut), first described in *Ronaghi et al.* 1998: *A sequencing method based on real-time pyrophosphate*". Science 281 (5375), 363-365. This technology uses an emulsion PCR in which single-stranded DNA binding beads are encapsulated by vigorous vortexing into aqueous micelles containing PCR reactants surrounded by oil for emulsion PCR amplification. During the pyrosequencing process, light emitted from phosphate molecules during nucleotide incorporation is recorded as the polymerase synthesizes the DNA strand.

2) The sequencing-by-synthesis approaches developed by Solexa (now part of Illumina Inc., San Diego, California) which is based on reversible dye-terminators and implemented e.g. in the Illumina/Solexa Genome Analyzer™ and in the Illumina HiSeq 2000 Genome Analyzer™. In this technology, all four nucleotides are added simultaneously into oligo-primed cluster fragments in flow-cell channels along with DNA polymerase. Bridge amplification extends cluster strands with all four fluorescently labeled nucleotides for sequencing.

3) Sequencing-by-ligation approaches, e.g. implemented in the SOLid™ platform of Applied Biosystems (now Life Technologies Corporation, Carlsbad, California). In this technology, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. As a second example, the Polonator™ G.007 platform of Dover Systems (Salem, New Hampshire) also employs a sequencing-by-ligation approach by using a randomly arrayed, bead-based, emulsion PCR to amplify DNA fragments for parallel sequencing.

4) Single-molecule sequencing technologies such as e.g. implemented in the PacBio RS system of Pacific Biosciences (Menlo Park, California) or in the HeliScope™ platform of Helicos Biosciences (Cambridge, Massachusetts). The distinct characteristic of this technology is its ability to sequence single DNA or RNA molecules without amplification, defined as Single-Molecule Real Time (SMRT) DNA sequencing. For example, HeliScope uses a highly sensitive fluorescence detection system to directly detect each nucleotide as it is synthesized. A similar approach based on fluorescence resonance energy transfer (FRET) has been developed from Visigen Biotechnology (Houston, Texas). Other fluorescence-based single-molecule techniques are from U.S. Genomics (GeneEngine™) and Genovoxx (AnyGene™).

5) Nano-technologies for single-molecule sequencing in which various nanostructures are used which are e.g. arranged on a chip to monitor the movement of a polymerase molecule on a single strand during replication. Non-limiting examples for approaches based on nano-technologies are the GridON™ platform of Oxford Nanopore Technologies (Oxford, UK), the hybridization-assisted nano-pore sequencing (HANS™) platforms developed by Nabsys (Providence, Rhode Island), and the proprietary ligase-based DNA sequencing platform with DNA nanoball (DNB) technology called combinatorial probe-anchor ligation (cPAL™).

6) Electron microscopy based technologies for single-molecule sequencing, e.g. those developed by Light-Speed Genomics (Sunnyvale, California) and Halcyon Molecular (Redwood City, California)

7) Ion semiconductor sequencing which is based on the detection of hydrogen ions that are released during the polymerisation of DNA. For example, Ion Torrent Systems (San Francisco, California) uses a high-density array of micro-machined wells to perform this biochemical process in a massively parallel way. Each well holds a different DNA template. Beneath the wells is an ion-sensitive layer and beneath that a proprietary Ion sensor.

The term "nucleic acid", as used herein, is intended to include deoxyribonucleic acid (DNA) or ribonucleic acid (RNA) such as cDNA, mRNA, recombinantly produced and chemically synthesized molecules. A nucleic acid may be single-stranded or double-stranded. According to the invention, RNA includes in vitro transcribed RNA (IVT RNA) or synthetic RNA. According to the invention, a nucleic acid is preferably an isolated nucleic acid. Furthermore, the nucleic acids described herein may be recombinant molecules.

The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e., transfection of, cells, for example, in the form of RNA which can be prepared by in vitro transcription from a DNA template. The RNA can moreover be modified before application by stabilizing sequences, capping, and polyadenylation.

In the context of the present invention, the term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a β-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally-occurring DNA.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially or completely purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA. According to the present invention, the term "RNA" includes and preferably relates to "mRNA" which means "messenger RNA" and relates to a transcript which may be produced using DNA as template and encodes a peptide or protein. mRNA typically comprises a 5' non translated region (5'-UTR), a protein or peptide coding region and a 3' non translated region (3'-UTR). mRNA has a limited halftime in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. In order to increase expression of the RNA used according to the present invention, it may be modified within the coding region, i.e., the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5-cap analog that resembles the RNA cap structure and is modified to possess the ability to stabilize RNA and/or enhance translation of RNA if attached thereto, preferably in vivo and/or in a cell.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e., downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The nucleic acids described herein may be comprised in a vector which can be used to deliver a nucleic acid to the interior of a cell. The term "vector" as used herein includes any vectors known to the skilled person including plasmid vectors, cosmid vectors, phage vectors such as lambda phage, viral vectors such as adenoviral or baculoviral vectors, retro- or lentiviral vectors, transposons or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

Those of skill in the art of molecular biology generally know how to use promoters, enhancers, and cell type combinations for protein expression. The promoters employed may be constitutive, tissue-specific, inducible, and/or useful under the appropriate conditions to direct high level expression of the introduced nucleic acid segment. The promoter may be heterologous or endogenous. Constitutive promoter sequences which may be used according to the invention, include, but are not limited to the immediate early cytomegalovirus (CMV) promoter sequence, the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

Nucleic acids can be transferred into a host cell by physical, chemical or biological means.

Physical methods for introducing a nucleic acid into a host cell include calcium phosphate precipitation, lipofection, particle bombardment, microinjection, electroporation, and the like.

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

"Encoding" refers to the inherent property of specific sequences of nucleotides in a nucleic acid to serve as templates for synthesis of other polymers and macromolecules in biological processes having either a defined sequence of nucleotides or a defined sequence of amino acids. Thus, a nucleic acid encodes a protein if expression (translation and optionally transcription) of the nucleic acid produces the protein in a cell or other biological system.

The term "expression" is used according to the invention in its most general meaning and comprises the production of RNA and/or peptides or polypeptides, e.g. by transcription and/or translation. With respect to RNA, the term "expression" or "translation" relates in particular to the production of peptides or polypeptides. It also comprises partial expression of nucleic acids. Moreover, expression can be transient or stable.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide or polypeptide.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

According to the invention it is preferred that a nucleic acid such as RNA encoding a peptide or protein once taken up by or introduced, i.e., transfected or transduced, into a cell which cell may be present in vitro or in a subject results in expression of said peptide or protein. The cell may express the encoded peptide or protein intracellularly (e.g. in the cytoplasm and/or in the nucleus), may secrete the encoded peptide or protein, or may express it on the surface.

According to the invention, terms such as "nucleic acid expressing" and "nucleic acid encoding" or similar terms are used interchangeably herein and with respect to a particular peptide or polypeptide mean that the nucleic acid, if present in the appropriate environment, preferably within a cell, can be expressed to produce said peptide or polypeptide.

Terms such as "transferring", "introducing", "transfecting" or "transducing" are used interchangeably herein and relate to the introduction of nucleic acids, in particular exogenous or heterologous nucleic acids, such as RNA into a cell. According to the present invention, the cell can be present in vitro or in vivo, e.g. the cell can form part of an organ, a tissue and/or an organism, According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cell lines allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

According to the present invention, the term "peptide" refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds.

The term "protein" refers to large peptides, i.e., polypeptides, preferably to peptides with more than 100 amino acid residues, but in general the terms "peptide", "polypeptide" and "protein" are synonyms and are used interchangeably herein.

According to the invention, the term "modification" with respect to peptides, polypeptides or proteins relates to a sequence change in a peptide, polypeptide or protein compared to a parental sequence such as the sequence of a wildtype peptide, polypeptide or protein. The term includes amino acid insertion variants, amino acid addition variants, amino acid deletion variants and/or amino acid substitution variants, preferably amino acid substitution variants. All these sequence changes according to the invention may potentially create new epitopes.

For the purposes of the present invention, "variants" of an amino acid sequence comprise amino acid insertion variants, amino acid addition variants, amino acid deletion variants and/or amino acid substitution variants.

Amino acid insertion variants comprise insertions of single or two or more amino acids in a particular amino acid sequence.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. Amino acid deletion variants that comprise the deletion at the N-terminal and/or C-terminal end of the protein are also called N-terminal and/or C-terminal truncation variants.

Amino acid substitution variants are characterized by at least one residue in the sequence being removed and another residue being inserted in its place.

Preferably the degree of similarity, preferably identity between a given amino acid sequence and an amino acid sequence which is a variant of said given amino acid sequence or which is modified with respect to said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. The degree of similarity or identity is given preferably for a segment of at least 80, at least 100, at least 120, at least 150, at least 180, at least 200 or at least 250 amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "% identity" is intended to refer, in particular, to a percentage of amino acid residues which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2,482, with the aid of the local homology algorithm by Neddleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

Homologous amino acid sequences exhibit according to the invention at least 40%, in particular at least 50%, at least 60%, at least 70%, at least 80%, at least 90% and preferably at least 95%, at least 98% or at least 99% identity of the amino acid residues.

A nucleic acid sequence which is at least 90% identical to a reference nucleic acid sequence includes nucleic acid sequences which are at least 91%, at least 92%, at least 93%, at least 94%, at least 95%, at least 96%, at least 97%, at least 98%, or at least 99% identical to a reference nucleic acid sequence.

According to the invention, a variant, fragment, part or portion of an amino acid sequence, peptide or protein preferably has a functional property of the amino acid sequence, peptide or protein, respectively, from which it has been derived, i.e., it is functionally equivalent. In one embodiment, a variant, fragment, part or portion of an amino acid sequence, peptide or protein is immunologically equivalent to the amino acid sequence, peptide or protein, respectively, from which it has been derived. In one embodiment, the functional property is an immunological property.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

The term "derived" means according to the invention that a particular entity, in particular a particular sequence, is present in the object from which it is derived, in particular an organism or molecule. In the case of amino acid or nucleic acid sequences, especially particular sequence regions, "derived" in particular means that the relevant amino acid sequence or nucleic acid sequence is derived from an amino acid sequence or nucleic acid sequence in which it is present. The term "cell" or "host cell" preferably is an intact cell, i.e., a cell with an intact membrane that has not released its normal intracellular components such as enzymes, organelles, or genetic material. An intact cell preferably is a viable cell, i.e., a living cell capable of carrying out its normal metabolic functions. Preferably said term relates according to the invention to any cell which can be transformed or transfected with an exogenous nucleic acid. The term "cell" includes according to the invention prokaryotic cells (e.g., *E. coli*) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines.

A cell which comprises a nucleic acid, e.g. which has been transfected with a nucleic acid, preferably expresses the peptide or protein encoded by the nucleic acid.

The term "expansion" refers to a process wherein a specific entity is multiplied. In one embodiment of the present invention, the term is used in the context of an immunological response in which lymphocytes are stimulated by an antigen, proliferate, and the specific lymphocyte recognizing said antigen is amplified. Preferably, clonal expansion leads to differentiation of the lymphocytes.

"Isolated" as used herein, is intended to refer to a molecule which is substantially free of other molecules such as other cellular material.

In particular, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The term "recombinant" in the context of the present invention means "made through genetic engineering". Preferably, a "recombinant object" such as a recombinant cell or nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

Terms such as "reducing", "inhibiting" or "decreasing" relate to the ability to cause an overall decrease, preferably of 5% or greater, 10% or greater, 20% or greater, more preferably of 50% or greater, and most preferably of 75% or greater, in the level. These terms include a complete or essentially complete inhibition, i.e., a reduction to zero or essentially to zero.

Terms such as "increasing", "enhancing", "promoting", or "stimulating" relate to the ability to cause an overall increase, preferably of 5% or greater, 10% or greater, 20% or greater, 50% or greater, 75% or greater, 100% or greater, 200% or greater, or 500% or greater, in the level. These terms may relate to an increase, enhancement, promotion, or stimulation from zero or a non-measurable or non-detectable level to a level of more than zero or a level which is measurable or detectable. Alternatively, these terms may also mean that there was a certain level before an increase, enhancement, promotion, or stimulation and after the increase, enhancement, promotion, or stimulation the level is higher.

The agents, compositions, and immunotherapeutic approaches described herein can be used to treat a subject with a disease, e.g., a disease characterized by the presence of an antigen or diseased cells expressing an antigen. Particularly preferred diseases are cancer diseases. Agents and compositions described herein may also be used for immunization or vaccination to prevent a disease described herein.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes infectious diseases and cancer diseases. Any reference herein to cancer or particular forms of cancer also includes cancer metastasis thereof.

A disease to be treated according to the invention is preferably a disease involving an antigen or being associated with an antigen.

The term "disease associated with an antigen" or "disease involving an antigen" refers to any disease which implicates an antigen, e.g. a disease which is characterized by the presence of an antigen or cells expressing an antigen. The disease involving an antigen can be an infectious disease, or a cancer disease or simply cancer. As mentioned above, the antigen may be a disease-associated antigen, such as a tumor-associated antigen, a viral antigen, or a bacterial antigen.

The term "infectious disease" refers to any disease which can be transmitted from individual to individual or from organism to organism, and is caused by a microbial agent. Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. *chlamydia* or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing a tumor antigen and a cancer cell expresses a tumor antigen.

In one embodiment, a cancer disease is a malignant disease which is characterized by the properties of anaplasia, invasiveness, and metastasis. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e., a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "treatment" or "therapeutic treatment" relates to any treatment which is intended to improve the health status and/or to prolong (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual, in particular an individual being at risk for the disease. The terms "prophylactic treatment" or "preventive treatment" are used herein interchangeably.

By "being at risk" is meant a subject, i.e., a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The terms "immunization" or "vaccination" describe the process of providing an antigen to an individual with the purpose of inducing an immune response, for example, for therapeutic or prophylactic reasons.

The term "in vivo" relates to the situation in a subject.

The term "individual" or "subject" relates to vertebrates, particularly mammals. For example, mammals in the context of the present invention are humans, non-human primates, domesticated mammals such as dogs, cats, sheep, cattle, goats, pigs, horses etc., laboratory animals such as mice, rats, rabbits, guinea pigs, etc. as well as animals in captivity such as animals of zoos. The term "subject" also relates to non-mammalian vertebrates such as birds (particularly domesticated birds such as chicken, ducks, geese, turkeys) and to fish (particularly farmed fish, e.g. salmon or catfish). The term "animal" as used herein also includes humans. Preferably, the term "patient" relates to a diseased individual.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The agents for immunotherapy described herein may be administered in the form of any suitable pharmaceutical composition. The term "pharmaceutical composition" relates to a formulation comprising a therapeutically effective agent or a salt thereof, preferably together with pharmaceutical excipients such as buffers, preservatives and tonicity modifiers. Said pharmaceutical composition is useful for treating or preventing a disease or disorder by administration of said pharmaceutical composition to an individual. A pharmaceutical composition is also known in the art as a pharmaceutical formulation. The pharmaceutical composition can be administered locally or systemically.

The term "systemic administration" refers to the administration of a therapeutically effective agent such that the agent becomes widely distributed in the body of an individual in significant amounts and develops a biological effect. According to the present invention, it is preferred that administration is by parenteral administration.

The term "parenteral administration" refers to administration of a therapeutically effective agent such that the agent does not pass the intestine. The term "parenteral administration" includes intravenous administration, subcutaneous administration, intradermal administration or intraarterial administration but is not limited thereto.

The agents for immunotherapy described herein may be administered in combination with one or more adjuvants. Such adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples for adjuvants include saponins, incomplete Freund's adjuvants, complete Freund's adjuvants, tocopherol or alum, but are not limited thereto.

The pharmaceutical composition according to the present invention is generally applied in a "pharmaceutically effective amount" and in "a pharmaceutically acceptable preparation".

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The term "pharmaceutically acceptable" refers to the non-toxicity of a material which does not interact with the action of the active component of the pharmaceutical composition.

The pharmaceutical compositions of the present invention may contain salts, buffers, preserving agents, carriers and optionally other therapeutic agents. Preferably, the pharmaceutical compositions of the present invention comprise one or more pharmaceutically acceptable carriers, diluents and/or excipients.

The term "excipient" is intended to indicate all substances in a pharmaceutical composition which are not active ingredients such as binders, lubricants, thickeners, surface active agents, preservatives, emulsifiers, buffers, flavoring agents, or colorants.

The term "diluent" relates a diluting and/or thinning agent. Moreover, the term "diluent" includes any one or more of fluid, liquid or solid suspension and/or mixing media.

The term "carrier" relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol and water.

According to the invention, nucleic acid such as RNA may be administered formulated in carriers or delivery vehicles such as in a nanoparticulate formulation, in particular a lipoplex formulation. Pharmaceutical carriers, excipients or diluents can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

In one embodiment, the composition is an aqueous composition. The aqueous composition may optionally comprise solutes, e.g. salts. In one embodiment, the composition is in the form of a freeze-dried composition. A freeze-dried composition is obtainable by freeze-drying a respective aqueous composition.

The agents and compositions provided herein may be used alone or in combination with other therapeutic regimens such as surgery, irradiation, chemotherapy and/or bone marrow transplantation (autologous, syngeneic, allogeneic or unrelated).

The present invention is described in detail and is illustrated by the figures and examples, which are used only for illustration purposes and are not meant to be limiting. Owing to the description and the examples, further embodiments which are likewise included in the invention are accessible to the skilled worker.

FIGURES

FIG. 1—B2M deletion/inversion event on chromosome 15. (A) Schematic overview of genomic region in wild-type genome. (B) Detailed drawing of mutated locus before and after deletion/inversion including primer sites. The legend is given in the bottom left panel.

Figure 2:
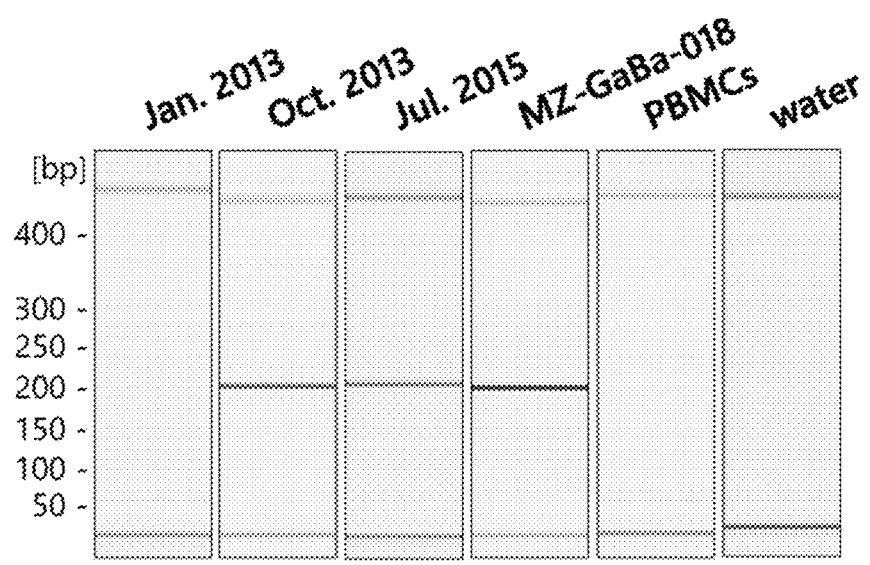

FIG. 2—Exemplary Image of capillary electrophoresis of PCR products (primer pair MZGaBa_S2aP1). The product in the PCR reactions of the metastases from October 2013 and July 2015 and MZ-GaBa-018 confirms the assumed deletion/inversion event and its presence in the patient already before IVAC MUTANOME treatment (PBMC: autologous peripheral blood mononuclear cells, i.e. germline control).

FIG. 3—TaqMan® assay MZGaBa_LCM_P4_FRP. The assay uses the primer pair MZGaBa_LCM_P4. The probe MZGaBa_LCM_P4_P is placed asymmetrically over the fusion site (30/6 bp).

FIG. 4—TaqMan® Assay MZGaBa_MaSu_m_FRP. New primers were designed for this assay that allow to place the probe MZGaBa_MaSu_m_P more symmetrically over the fusion site (22/15 bp).

EXAMPLES

The techniques and methods used herein are described herein or carried out in a manner known per se and as described, for example, in Sambrook et al., Molecular Cloning: A Laboratory Manual, 2$^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Materials and Methods

Bioinformatics Methods

RNA and exome sequencing (50 bp, paired-end, Illumina HiSeq 2500) were performed on the tumor cell line MZ—GaBa-018, derived from melanoma patient PA018, who obtained IVAC MUTANOME (NCT02035956) treatment, on three metastases of PA018 that were excised in January 2013, October 2013 (both pre-treatment) and July 2015 (post-treatment) and on the patient's PBMCs. MZ-GaBa-018 was established from the latest metastasis. RNA and exome sequencing reads were applied to the in-house standard pipeline for mutation detection and expression analysis, which included the alignment of the exome sequencing reads to the reference genome hg19 using BWA (Li HI, Durbin R, 2009, Bioinformatics 25, 1754-60). Whole genome sequencing (100 bp, paired-end, Illumina HiSeq 2500) was performed on MZ-GaBa-018 and the patient's PBMCs and the reads were aligned to hg19 using hisat2 version 2.0.1-beta (Kim D et al., 2015, Nat Methods 12, 357-60).

The deletion of the B2M locus was detected and the deletion start point upstream of B2M was defined by manual curation of the exome alignments of MZ-GaBa-018 in the Integrative Genomics Viewer (IGV; Thorvaldsdóttir H. et al., 2013, Brief Bioinform. 14, 178-92). Split read and discordant paired-end alignments were used to deduce the deletion end point. In addition, exome reads were applied to de novo assembly using Trinity (Zhao Q Y et al., 2011, BMC Bioinformatics 12 Suppl 14:S2). Split reads and contig sequences from the de novo assembly were used to design primers with NCBI Primer-BLAST (Yc J et al., 2012, BMC Bioinformatics 13:134) to detect the deletion via PCR in the cell line, the patient's metastases and unrelated cancer patients.

DNA Extraction (MZ-GaBa-018 Cell Line)

DNA was extracted from 5×10$^6$ cells of MZ-GaBa-018 cell line using Dneasy®, Blood & Tissue Kit (QIAGEN, Cat. No. 69504) according to the manufacturer's manual. The eluted DNA was diluted to a concentration of 1 ng/μl for any following PCR.

DNA Extraction (FFPE Melanoma Samples)

Of 20 FFPE melanoma samples 3 curls with 10 μm thickness each were cut for subsequently DNA extraction using, Maxwell® RSC DNA FFPE Kit "(Promega, art. no. AS1450) and the Maxwell® RSC instrument. The eluted DNA was then quantified with the, QuBit™ dsDNA HS Assay Kit" (Invitrogen. art. No. Q32854) and concentrations are given in Table 1.

TABLE 1

Concentrations of DNA extractions from unrelated FFPE melanoma samples determined by QuBit ™.

| Sample ID | Concentration |
| --- | --- |
| BT004345-DNA-01-A | 15.3 ng/μl |
| BT004346-DNA-01-A | 22.6 ng/μl |
| BT004347-DNA-01-A | 7.8 ng/μl |
| BT004348-DNA-01-A | 22.1 ng/μl |
| BT004349-DNA-01-A | 8.0 ng/μl |
| BT004350-DNA-01-A | 1.6 ng/μl |
| BT004351-DNA-01-A | 8.0 ng/μl |
| BT004352-DNA-01-A | 38.4 ng/μl |
| BT004353-DNA-01-A | 1.9 ng/μl |
| BT004354-DNA-01-A | 4.9 ng/μl |
| BT004369A_1F_1PEB-DNA-01-A | 57.3 ng/μl |
| BT004370A_1F_1PEB-DNA-01-A | 47.3 ng/μl |
| BT004371A_1F_1PEB-DNA-01-A | 72.1 ng/μl |
| BT004372A_1F_1PEB-DNA-01-A | 57.7 ng/μl |
| BT004373A_1F_1PEB-DNA-01-A | 23.1 ng/μl |
| BT004374A_1F_1PEB-DNA-01-A | 14.8 ng/μl |
| BT004375A_1F_1PEB-DNA-01-A | 13.9 ng/μl |
| BT004376A_1F_1PEB-DNA-01-A | 6.6 ng/μl |
| BT004377A_1F_1PEB-DNA-01-A | 18.4 ng/μl |
| BT004378A_1F_1PEB-DNA-01-A | 7.3 ng/μl |

Quantitative SYBR® Green Real-Time PCR (qRT-PCR)

The DNA was analysed for presence of the B2M deletion event described in FIG. 1 using qRT-PCR on the 96-Well Applied Biosystems 7300 Real-Time PCR System. For the detection of the deletion/inversion event SYBR® Green qRT-PCR and primer pairs "MZGaBa_LCM_P4" and "MZGaBa_PATL2_2" were used with the following run conditions—Initiation temperature of 95° C. for 15 minutes followed by 40 cycles of PCR using 950 for 30 seconds for denaturation, annealing step at 60° C. for 30 seconds and elongation with a temperature of 72° C. for 30 seconds.

Fluorescence was measured after each PCR cycle. After 40 cycles qRT-PCR a dissociation stage was performed.

The reactions were run using 2× QuantiTect SYBR® Green PCR Kit (QIAGEN cat. no. 204145) in an overall volume of 30.0 µl, consisting 15.0 µl mastermix, 10.5 µl water, 2 µl primer pair (forward % reverse primer each @ 10 µM) and 2.5 µl sample DNA (diluted to 1 ng/µl). For the analysis of qRT-PCR data a threshold of 0.5 and manual baseline was selected.

Quantitative TaqMan® Assay Real-Time PCR (qRT-PCR)

The DNA was analysed for presence of the B2M deletion event described in FIG. 1 using qRT-PCR (quantitative Real-Time PCR) on the 96-Well Applied Biosystems 7300 Real-Time PCR System. For the detection of the Deletion/Inversion event two FAM-BHQ1 labelled TaqMan® assays "MZGaBa_LCM_P4_FRP" and "MZGaBa_Ma-Su_m_FRP" were used in qRT-PCR using the following run conditions—Initiation temperature of 95° C. for 30 seconds followed by 50 cycles of two-step PCR where the melting temperature is 95' for 3 seconds with subsequent annealing/elongation temperature of 60° C. for 30 seconds. FAM-fluorescence was measured after each two-step PCR cycle. The reactions were run using 2× PerfeCTa® qPCR Fast-Mix®, UNG, ROX (Quanta BioSciences art. no. 95077-05K) in an overall volume of 30.0 µl, consisting 15.0 µl mastermix, 11.5 µl water, 1.5 µl 20× TaqMan® assay (18 µM forward/reverse primer+5 µM probe) and 2.0 µl sample DNA.

For the analysis of qRT-PCR data a threshold of 0.25 and manual baseline with start cycle 3 and end cycle 25 was selected.

Example 2: Identification of a Chromosomal Deletion and Inversion Event in Chromosome 15 Resulting in a Loss of MHC Class I Expression The tumor cell line MZ-GaBa-018, derived from a post-treatment metastasis of melanoma patient PA018, completely lacks MHC class I expression on tumor cell surface as determined via flow cytometry. HLA class I gene transcription (RPKM values HLA-A=279, HLA-B=207, HLA-C=292) was verified in NGS RNA sequencing data of MZ-GaBa-018, but no transcripts were detected for B2M (RPKM B2M=0). The corresponding exome data revealed that the complete B2M locus is deleted. The deletion starts after position chr15:44,962,085 in an intron in the PATL2 locus upstream of B2M well covered in the exome capture. The deletion end point is located more than 200kb downstream at position chr15:45,166,582. Moreover, the deletion is followed by an inversion of the sequence downstream of the deleted region. Whole genome sequencing of MZ-GaBa-018 reveals the exact intergenic end point of the deletion, which represents the start point of the inverted region (chr15:45,166,583-chr15:45,304,626). The hg19 reference sequence of the relevant genomic region (chr15:44,961,686-45,304,927) is given in sequence 01. The sequence of the rearranged genomic region is given in sequence 02. A schematic overview of the observed deletion/inversion event is given in FIG. 1.

```
Sequence 01-Reference sequence hg19 (chr15:44,961,
686-45,304,927)
[...(chr15:44,962,387-45,166,282
(203,896 bp))(SEQ ID NO: 1)]
CCCTAAGGAACTGATATCTCACCTTCTCAATCCGGTATAATACCCGAAGC

CTCTGACTGCTTGCAGCTTCTATATCCTAGGAGAAGGGAGTCACCAGCTA

TCAGCTACACTGCCACTGCCACAGCCCTAGCCCAGGCCCCCAACTAGCTA

GAGATTGAGCTGGAAAGGCTAGAAACAAAGTCTGATCACACTTCTTCCTC

CTTCTTCGGTCACAGTCTTAAACACAAGAATGTTCTAGACCCTTCTTCCA

AAGGGGAGAGAAAAATGTCTGGGAAGATAGTGCTCCCACCTGCTCTTGAG

TTCCATGGGGTACCGCATCAATAGCTCGGCGAGGGCTGAAGCATGTCGAC

ACAGCTACCTGGCCCAGGGAACCCTCGATTCGGACCACTGCATGAGAAGA

GAGGCACATTTCCTTCCCCCTCCCACACTCTGTCCACCCAGATGCCCAGC

CCAAGTCAGCAGGTCAGCCCTGACCCTACCGGACTCATAAGCCTCTGCCT

TCGGAATGTAAGGCGTTACCAGCTTGAGGGACTCAACCCGGTTTCTTCGT

CCAAGTAGCTCTTCGTCTGCCTGCTTCTTCTCTAGCTTCTGGTAATATTC

CTGAGAATGCACGGAATAGGAAACAAAAAAACAAAACACCTTATATTCAT

CTTTTGAATTTAGAATTAAGTTTCTCAAGTGCAGCCTCTTAAGTTTAGTT

T

[...(chr15:45,166,884-45,304,326
(137,444 bp))(SEQ ID NO: 2)]
TC

TCCAAGTGAGGTCGAAGTTTTGCCCTAGACCCTGTAGGACATCTATATAC

CTATCAGGATCATCTGAAAACTTCCCCAGATCTACCTTGATCTGCTTTAA

ATCAGAGAGGGAGAAGGGGACATGTACCCAGGTTGGGCCAAATTCCCCTC

CCCCTACAGCTTGAAAAGAACATAACCAATAGCCCAGAGGTTTTTGTGGC

CCCTTGGAGATTTCTTTGCTTGTTTCCTTCTGGGTGGGGAGATTAGAGG

AGGCTCATCATTAATAGGAAGAGGAGCTGTAGGGAGGCTAGGATATGGGG

GTAAGCTGAGAGGTCCTCCTGTGGAATGTAGGTTGCAAGCTTTGCATAGT

TGTGGATTGTCCTTCAGTGAAAAGAAAGCTTGGACATAAGGTATTTCACT

CCATTTGCCTTCCATCTTACAGAAAAAGTCAAGCTGCAGGATAATACTGT

AATTTATACTTTCCACAGGTGGCCATTTTTCCCTATCAGAGAGAGAATAT

TGGGACCAGGCCACAGTGCAGAAAAAAATAAGCCTCTTCTTTTTCAGGGC

TTGCAGGTCAAATTCATCCCAATGGCTTAGGATGCATTTCAAGTGTGAG (SEQ ID NO: 3)
CCA

CCTGAGGGACGTATAAATTACAATAGTATCCTGCAGCTTGAACTTTTCTG

TAAGAAGGAAGGCAAGTGGAGTGAAATACCTTATGTCCAAGCTTTCTTTT

CACTGAAGGACAATCCACAACTATGCAAAGCTTGCAATCTACATTCCACA

GGAGGACCTCTCAGCTTACCCCCATATCCTAGCCTCCTTACAGCTCCTCT

TCCTTCCTATTAATGATGAGCCTCCTCTAATCTCCCCCACCCAGAAGGAA

ACAAGCAAAGAAATCTCCAAGGGACCACAAAAAACCCGCTATAGGTTATG

TCCTCTTCAAGCTGTAGGGGAGGGAATTTGGCCCAACCCGGGTACAAG

TCCCCTTCTCCCTCTCTGATTTAAAGCAGATCAAGTTAGATCTGGGGAAG

TTTTCAGGTGATCCTGATAGGTATATAGATATCCTATGGGGTCTAGGGCA

AACCTTCGACCTCACTTGGAGAGATGTCATGCTATTGTTTTGTTGCTGTT

GTTGTTGTTTTGAGATGGAGTTTCACTCTGTTGCCCAGGCTGGAGTGCAG

TGGCACAATCTCAGCTCACTGCAAGCTCCACTTCCCGGGTTCACACCA
```

-continued

Sequence 02-Sequence containing deletion/inversion
event (positions 1-400, 1602-1003 [inverted] and
1603-1903 of sequence 01).
[...(chr15:45,304,326-45,166,884
(137,444 bp)) (SEQ ID NO: 4)]

CCCTAAGGAACTGATATCTCACCTTCTCAATCCGGTATAATACCCGAAGC

CTCTGACTGCTTGCAGCTTCTATATCCTAGGAGAAGGGAGTCACCAGCTA

TCAGCTACACTGCCACTGCCACAGCCCTAGCCCAGGCCCCCAACTAGCTA

GAGATTGAGCTGGAAAGGCTAGAAACAAAGTCTGATCACACTTCTTCCTC

CTTCTTCGGTCACAGTCTTAAACACAAGAATGTTCTAGACCCTTCTTCCA

AAGGGGAGAGAAAAATGTCTGGGAAGATAGTGCTCCCACCTGCTCTTGAG

TTCCATGGGGTACCGCATCAATAGCTCGGCGAGGGCTGAAGCATGTCGAC

ACAGCTACCTGGCCCAGGGAACCCTCGATTCGGACCACTGCATGAGAAGA

AACCTATAGCGGGTTTTTTGTGGTCCCTTGGAGATTTCTTTGCTTGTTTC

CTTCTGGGTGGGGAGATTAGAGGAGGCTCATCATTAATAGGAAGGAAGA

GGAGCTGTAAGGAGGCTAGGATATGGGGGTAAGCTGAGAGGTCCTCCTGT

GGAATGTAGATTGCAAGCTTTGCATAGTTGTGGATTGTCCTTCAGTGAAA

AGAAAGCTTGGACATAAGGTATTTCACTCCACTTGCCTTCCTTCTTACAG

AAAAGTTCAAGCTGCAGGATACTATTGTAATTTATACGTCCCTCAGGTGG

CTC                                                 (SEQ ID NO: 5)

ACACTTGAAATGCATCCTAAGCCATTGGGATGAATTTGACCTGCAAGCCC

TGAAAAAGAAGAGGCTTATTTTTTCTGCACTGTGGCCTGGTCCCAATAT

TCTCTCTCTGATAGGGAAAAATGGCCACCTGTGGAAAGTATAAATTACAG

TATTATCCTGCAGCTTGACTTTTTCTGTAAGATGGAAGGCAAATGGAGTG

AAATACCTTATGTCCAAGCTTTCTTTTCACTGAAGGACAATCCACAACTA

TGCAAAGCTTGCAACCTACATTCCACAGGAGGACCTCTCAGCTTACCCCA

TGTCCTCTTCAAGCTGTAGGGGAGGGGAATTTGGCCCAACCCGGGTACA

AGTCCCCTTCTCCCTCTCTGATTTAAAGCAGATCAAGTTAGATCTGGGGA

AGTTTTCAGGTGATCCTGATAGGTATATAGATATCCTATGGGGTCTAGGG

CAAACCTTCGACCTCACTTGGAGAGATGTCATGCTATTGTTTTGTTGCTG

TTGTTGTTGTTTTGAGATGGAGTTTCACTCTGTTGCCCAGGCTGGAGTGC

AGTGGCACAATCTCAGCTCACTGCAAGCTCCACTTCCCGGGTTCACACCA

The inverted region is flanked by long terminal repeats (LTR) of the ERV1 family (HERV9-int at positions chr15: 45,164,500-45,168,097 and chr15:45,302,994-45,304,836), which might have mediated the inversion. Thus, the observed event might be the result of a conserved mechanism, which could be found in further patients.

Primers were designed around the breakpoint at chr15: 44,962,085 for the detection of the transition from the PATL2 locus to the inverted sequence. The primers MZGaBa_S2aP1 (forward: 5'-AGCAT-GrCGACACAGCrACC-3' (SEQ ID NO: 15), reverse: 5'-ACCTCTCAGCTTACCCCCAT-3" (SEQ ID NO: 16)) amplifying a PCR product of 180 bp length are located at positions 340-359 and 523-542 in sequence 02. This primer pair is considered specific for this event as both primers would anneal on the same strand and their distance on a wild-type human genome is too large. One potential side product is reported by NCBI Primer-Blast (https://www.ncbi.nlm.nih.gov/tools/primer-blast/), which requires 4 mismatches per primer and has a length of 2290 bp, which is easily distinguishable from the intended PCR product of 180 bp. For a control reaction, a primer pair annealing at the PATL2 locus upstream of the deletion was designed. The primers MZGaBa_PATL2_2 (forward: 5'-ATGCAGCGA-TACCAGTTGCT-3' (SEQ ID NO: 25), reverse: 5'-GGAAAGCACCAAATGCCGAG-3' (SEQ ID NO: 26)) amplify a PCR product of 123 bp length (chr15:44,959,342-44,959,464).

To finally confirm the deletion/inversion event in MZ-GaBa-018 via PCR, the PCR product was applied to Sanger sequencing. The sequence retrieved by Sanger sequencing is shown in sequence 03.

Sequence 03-Sanger sequencing results using primer
pair MZGaBa_S2aP1 in MZ-GaBa-018.
                                                    (SEQ ID NO: 7)
TACAGCATGTCGACACAGCTACCTGGCCCAGGGAACCCTCGATTCGGACC ACTGCATGAGAAGAAAAtCTATAGCGGGTTTTTTGTGGTCCCTTGGAGAT TTCTTTGCTTGTTTCCTTCTGGGTGGGGAGATTcGAGGAGGCTCATCTA

TTCATAGCAAGAACAGAGCGTAATACT

Searching for the sequence using UCSC blat (https://genome.ucsc.edu/cgi-bin/bgBlat) reveals a perfect match to chr15:44,962,025-44,962,085 on the plus-strand for the positions 4 to 64 of sequence 03 (table 2). The only two further hits for this sequence fraction achieve a maximum of 83.4% identity spanning up to 30 bp. The remaining sequence was more ambiguous, but the top ranking hit (score 78) achieves 98.8% identity spanning 80 bp on the minus-strand at chr15:45,304,544-45,304,623 (table 3). This confirms the deletion/inversion event as expected from the NGS data.

TABLE 2

Blast results for Sanger sequence 03 (positions 1-64).

| QUERY | SCORE | START | END | QSIZE | IDENTITY | CHRO | STRAND | START | END | SPAN |
| --- | --- | --- | --- | --- | --- | --- | --- | --- | --- | --- |
| S2aP1_C5R | 61 | 4 | 64 | 65 | 100.0% | 15 | + | 44962025 | 44962085 | 61 |
| S2aP1_C5R | 27 | 19 | 62 | 65 | 66.7% | 11 | − | 76126302 | 76126331 | 30 |
| S2aP1_C5R | 23 | 14 | 39 | 65 | 83.4% | 15 | − | 77208625 | 77208648 | 24 |

TABLE 3

Blast results for Sanger sequence 03 (positions 65-177). Only hits with a score of at least 61 are shown.

| QUERY | SCORE | START | END | QSIZE | IDENTITY | CHRO | STRAND | START | END | SPAN |
|---|---|---|---|---|---|---|---|---|---|---|
| S2aP1_C5R | 78 | 5 | 84 | 84 | 98.8% | 15 | − | 45304544 | 45304623 | 80 |
| S2aP1_C5R | 71 | 7 | 84 | 84 | 96.2% | 17 | − | 52365682 | 52365761 | 80 |
| S2aP1_C5R | 67 | 7 | 84 | 84 | 93.6% | 1 | − | 173339095 | 173339175 | 81 |
| S2aP1_C5R | 66 | 2 | 80 | 84 | 92.5% | Y | − | 6354421 | 6354502 | 82 |
| S2aP1_C5R | 66 | 2 | 80 | 84 | 92.5% | Y | + | 9513156 | 9513237 | 82 |
| S2aP1_C5R | 65 | 5 | 84 | 84 | 91.3% | 5 | − | 146382807 | 146382889 | 83 |
| S2aP1_C5R | 65 | 7 | 84 | 84 | 92.4% | 5 | − | 51695233 | 51695313 | 81 |
| S2aP1_C5R | 65 | 12 | 84 | 84 | 94.6% | 10 | − | 121645132 | 121645204 | 73 |
| S2aP1_C5R | 65 | 7 | 84 | 84 | 92.4% | 8 | + | 54053957 | 54054037 | 81 |
| S2aP1_C5R | 65 | 16 | 84 | 84 | 97.2% | 4 | + | 35864679 | 35864747 | 69 |
| S2aP1_C5R | 65 | 16 | 84 | 84 | 97.2% | 15 | + | 45166475 | 45166543 | 69 |
| S2aP1_C5R | 65 | 7 | 84 | 84 | 92.4% | 10 | + | 96530970 | 96531050 | 81 |
| S2aP1_C5R | 64 | 15 | 84 | 84 | 92.8% | 18 | + | 23817455 | 23817523 | 69 |
| S2aP1_C5R | 63 | 16 | 84 | 84 | 95.7% | 8 | − | 74820348 | 74820416 | 69 |
| S2aP1_C5R | 63 | 16 | 84 | 84 | 95.7% | 8 | − | 73302286 | 73302354 | 69 |
| S2aP1_C5R | 63 | 16 | 84 | 84 | 95.7% | 7 | − | 108941357 | 108941425 | 69 |
| S2aP1_C5R | 63 | 16 | 84 | 84 | 95.7% | 4 | − | 161585598 | 161585666 | 69 |
| S2aP1_C5R | 63 | 16 | 84 | 84 | 95.7% | 3 | − | 51886267 | 51886335 | 69 |
| S2aP1_C5R | 63 | 12 | 84 | 84 | 91.6% | 3 | − | 17818045 | 17818116 | 72 |
| S2aP1_C5R | 63 | 17 | 83 | 84 | 97.1% | 17 | − | 50652623 | 50652689 | 67 |
| S2aP1_C5R | 63 | 16 | 84 | 84 | 95.7% | 10 | − | 116798909 | 116798977 | 69 |
| S2aP1_C5R | 63 | 16 | 84 | 84 | 95.7% | 10 | − | 22429831 | 22429899 | 69 |
| S2aP1_C5R | 63 | 16 | 84 | 84 | 95.7% | 1 | − | 101966535 | 101966603 | 69 |
| S2aP1_C5R | 63 | 16 | 84 | 84 | 95.7% | 1 | − | 48905768 | 48905836 | 69 |
| S2aP1_C5R | 63 | 16 | 84 | 84 | 95.7% | X | + | 105428865 | 105428933 | 69 |
| S2aP1_C5R | 63 | 16 | 84 | 84 | 95.7% | 9 | + | 79108516 | 79108584 | 69 |
| S2aP1_C5R | 63 | 16 | 84 | 84 | 95.7% | 8 | + | 52209691 | 52209759 | 69 |
| S2aP1_C5R | 63 | 16 | 84 | 84 | 95.7% | 10 | + | 17058692 | 17058760 | 69 |
| S2aP1_C5R | 62 | 17 | 84 | 84 | 95.6% | 8 | − | 49147702 | 49147769 | 68 |
| S2aP1_C5R | 61 | 16 | 84 | 84 | 94.3% | 8 | − | 79061947 | 79062015 | 69 |
| S2aP1_C5R | 61 | 7 | 78 | 84 | 93.1% | 5 | − | 114328185 | 114328259 | 75 |
| S2aP1_C5R | 61 | 16 | 84 | 84 | 94.3% | 1 | − | 211397635 | 211397703 | 69 |
| S2aP1_C5R | 61 | 16 | 84 | 84 | 94.3% | X | + | 70719899 | 70719967 | 69 |
| S2aP1_C5R | 61 | 16 | 84 | 84 | 94.3% | 9 | + | 88770045 | 88770113 | 69 |
| S2aP1_C5R | 61 | 7 | 84 | 84 | 89.8% | 4 | + | 131768216 | 131768296 | 81 |
| S2aP1_C5R | 61 | 16 | 84 | 84 | 94.3% | 12 | + | 1824199 | 1824267 | 69 |
| S2aP1_C5R | 61 | 16 | 84 | 84 | 94.3% | 10 | + | 69448041 | 69448109 | 69 |
| S2aP1_C5R | 61 | 16 | 84 | 84 | 94.3% | 1 | + | 75209740 | 75209808 | 69 |

Manual evaluation of the Sanger traces additionally reveals the insertion of a single adenine at the breakpoint (A at position 65 in sequence 03) which was considered in further assay design. The primers were also applied to genomic DNA from the patient's metastases. PCR and Sanger sequencing confirms the event in one pre-treatment (October 2013) and the post-treatment metastasis as observed in the cell line, proving that the loss of B2M occurred already in the patient (FIG. 2).

Assuming that the detected deletion/inversion event is a consequence of a conserved mechanism putatively involving LTR-mediated rearrangements, new primers were designed. These amplify a shorter, but still specific sequence covering the deletion breakpoint to detect the event in unrelated FFPE melanoma samples, taking into account that the DNA might be of lower quality than the cell line's. The primers MZGaBa_LCM_P4 (forward: 5'-GAACCCTC-GATTCGGACCAC-3' (SEQ ID NO: 18), reverse: 5'-CCACCCAGAAGGAAACAAGC-3' (SEO ID NO: 19)) amplifying a PCR product of 94 bp length were located at positions 369-388 and 442-461 in sequence 02. This primer pair is considered specific for this event as both primers would anneal on the same strand and their distance on a wild-type human genome was too large. Potential side products reported by NBC1 Primer-Blast require at least 4 mismatches per primer and the shortest unwanted product would have a length of 318 bp, which is easily distinguishable from the intended PCR product of 94 bp. These primers were successfully established on MZ-GaBa-018.

Additionally, breakpoint-spanning TaqMan® assays were designed as shown in FIGS. 3 and 4. The assay MZGaBa_LCM_P4_FRP uses the primers MZGaBa_LCM_P4. For the assay MZGaBa_MaSu_m_FRP also new primers were designed (MZGaBa_MaSu_m) that allow to place the TaqMan® probe almost symmetrically over the fusion site. For the full probe sequence (36 bp) of probe MZGaBa_LCM_P4_P (5'-(FAM)-CAAGGGAC-CACAAAAAAACCCGCTATAGGTITTCTTC-(BHQ1)-3') (SEQ ID NO: 20), no significant similarity was found on human genome or transcriptome using NCBI Nucleotide BLAST (nBLAST, https://blast.nebi.nlm.nih.gov/Blast.cgi). The probe part binding between chr15:45,304,597 and chr15:45,304,626 covers 83.3% of the overall probe. On this partial sequence 100% coverage is only given for the expected locus on chromosome 15 according to nBLAST. For the complete probe sequence (37 bp) of probe MZGaBa_MaSu_m_P (5'-(FAM)-CACAAAAAACCCGC-TATAGGTTTTCTTCTCATGCAGT-(BHQ1)-3') (SEQ ID NO: 24), no significant similarity was found on human genome or transcriptome as determined with nBLAST. The probe design is intended to cover about 50% of both fusion sequences, resulting in the highest specificity of detecting only the fusion site, without binding to the wild-type genome.

Both TaqMan assays were applied in duplicates to MZ-GaBa-018 and 20 unrelated FFPE melanoma samples. A positive signal in at least 3 out of 4 reactions, using the two independent TaqMan® assays and negative signals in the corresponding water controls even after 50 cycles of qRT-PCR, were set as threshold for the detection of the B2M deletion/inversion event. Applying these criteria it is assumed for sample BT004378A_1F_1PEB-DNA-01-A to carry the B2M deletion/inversion event. The Ct-values are shown in table 4. The positive control cell line MZ-GaBa-018 resulted in an average Ct-value of 30.75.

TABLE 4

Results of TaqMan ® assays for sample BT004378A, positive control MZ-GaBa-018 and water control.

| Well position | Sample ID | Assay | Detector | Ct-value |
|---|---|---|---|---|
| G3 | BT004378A_1F_1PEB-DNA-01-A | MZGaBa_LCM_P4_FRP | FAM | 37.63 |
| G4 | BT004378A_1F_1PEB-DNA-01-A | MZGaBa_LCM_P4_FRP | FAM | 42.40 |
| H3 | BT004378A_1F_1PEB-DNA-01-A | MZGaBa_MaSu_m_FRP | FAM | Undetermined |
| H4 | BT004378A_1F_1PEB-DNA-01-A | MZGaBa_MaSu_m_FRP | FAM | 39.14 |
| G5 | MZ-GaBa-018 (positive control cell line) | MZGaBa_LCM_P4_FRP | FAM | 30.37 |
| G6 | MZ-GaBa-018 (positive control cell line) | MZGaBa_LCM_P4_FRP | FAM | 31.09 |
| H5 | MZ-GaBa-018 (positive control cell line) | MZGaBa_MaSu_m_FRP | FAM | 30.61 |
| H6 | MZ-GaB-a-018 (positive control cell line) | MZGaBa_MaSu_m_FRP | FAM | 30.93 |
| G10 | water | MZGaBa_LCM_P4_FRP | FAM | Undetermined |
| G11 | water | MZGaBa_LCM_P4_FRP | FAM | Undetermined |
| G12 | water | MZGaBa_LCM_P4_FRP | FAM | Undetermined |
| H10 | water | MZGaBa_MaSu_m_FRP | FAM | Undetermined |
| H11 | water | MZGaBa_MaSu_m_FRP | FAM | Undetermined |
| H12 | water | MZGaBa_MaSu_m_FRP | FAM | Undetermined |

The presence of this specific 132M deletion in an unrelated melanoma sample further implies a conserved mechanism. The established assays are suitable for the detection of this deletion/inversion event.

The invention claimed is:

1. A method for screening for a genotype for loss of antigen presentation via major histocompatibility complex (MHC) class I, comprising: obtaining a sample containing nucleic acid from a human subject, and identifying a chromosomal deletion and inversion event in a chromosome 15, wherein the deletion and inversion event results in the loss of the beta-2-microglobulin (B2M) locus, and wherein the presence of the chromosomal deletion and inversion event indicates that the human subject possesses a genotype for loss of antigen presentation via MHC class I, wherein the identifying comprises (i) amplifying a nucleic acid sequence comprising the sequence set forth in SEQ ID NO: 9 and/or a sequence complementary to SEQ ID NO: 9 to generate an amplification product, (ii) contacting a probe to the amplification product, and (iii) detecting hybridization of the probe to the amplification product.

2. The method of claim 1, wherein identifying a chromosomal deletion and inversion event in a chromosome 15 comprises detecting the presence or absence of a nucleic acid sequence comprising a sequence selected from the group consisting of:
(i) a sequence identifying a chromosomal deletion and inversion event in a chromosome 15, wherein the deletion and inversion event results in the loss of the beta-2-microglobulin (B2M) locus, and comprising the sequence set forth in SEQ ID NO: 9, the sequence set forth in SEQ ID NO: 9 surrounding the end point of the deletion, which is the start point of the inverted region,
(ii) the sequence set forth in SEQ ID NO: 17 or a portion thereof of at least 40 nucleotides comprising the sequence set forth in SEQ ID NO: 10,
(iii) the sequence set forth in SEQ ID NO: 21 or a portion thereof of at least 40 nucleotides comprising the sequence set forth in SEQ ID NO: 10,
(iv) a sequence complementary to the sequences set forth in any one of (i) to (iii), and
(v) a sequence which is at least 90% identical to the sequences set forth in any one of (i) to (iv), wherein detection of the nucleic acid sequence indicates the presence of a chromosomal deletion and inversion event in a chromosome 15 that is predictive of a genotype for loss of antigen presentation via MHC class I.

3. The method of claim 1, wherein identifying a chromosomal deletion and inversion event in a chromosome 15 comprises amplifying a nucleic acid sequence comprising a sequence selected from the group consisting of:
(i) a sequence identifying a chromosomal deletion and inversion event in a chromosome 15, wherein the deletion and inversion event results in the loss of the beta-2-microglobulin (B2M) locus, and comprising the sequence set forth in SEQ ID NO: 9, the sequence set forth in SEQ ID NO: 9 surrounding the end point of the deletion, which is the start point of the inverted region,
(ii) the sequence set forth in SEQ ID NO: 17 or a portion thereof of at least 40 nucleotides comprising the sequence set forth in SEQ ID NO: 10,
(iii) the sequence set forth in SEQ ID NO: 21 or a portion thereof of at least 40 nucleotides comprising the sequence set forth in SEQ ID NO: 10,
(iv) a sequence complementary to the sequences set forth in any one of (i) to (iii), and
(v) a sequence which is at least 90% identical to the sequences set forth in any one of (i) to (iv).

4. The method of claim 3, wherein the amplification is performed using a set of primers selected from: (a) a set comprising the sequences set forth in SEQ ID NO: 15 and SEQ ID NO: 16; (b) a set comprising the sequences set forth in SEQ ID NO: 18 and SEQ ID NO: 19; and (c) a set comprising the sequences set forth in SEQ ID NO: 22 and SEQ ID NO: 23.

5. A method for screening for a genotype for loss of antigen presentation via MHC class I, by identifying a chromosomal deletion and inversion event in a chromosome 15 resulting in the loss of the beta-2-microglobulin (B2M) locus comprising: obtaining a sample containing nucleic acid from a subject, hybridizing to the nucleic acid a group of primers, amplifying the hybridized group of primers, and detecting the presence or absence of an amplification product, wherein detection of the amplification product indicates the presence of a chromosomal deletion and inversion event in a chromosome 15 resulting in the loss of the beta-2-microglobulin (B2M) locus that is predictive of a genotype for loss of antigen presentation via MHC class I;
wherein the group of primers is selected from: (a) the group of primers comprising the sequences set forth in SEQ ID NO: 15 and SEQ ID NO: 16; (b) the group of primers comprising the sequences set forth in SEQ ID NO: 18 and SEQ ID NO: 19; and (c) the group of primers comprising the sequences set forth in SEQ ID NO: 22 and SEQ ID NO: 23.

6. The method of claim 5, wherein the group of primers is selected from (a) the group of primers comprising the sequences set forth in SEQ ID NO: 15 and SEQ ID NO: 16.

7. The method of claim 5, wherein the group of primers is selected from (b) the group of primers comprising the sequences set forth in SEQ ID NO: 18, and SEQ ID NO: 19.

8. The method of claim 7, wherein the amplification product has a length of 80 to 100 bp, preferably 90 to 95 bp, more preferably about 94 bp.

9. The method of claim 7, further comprising hybridizing to the nucleic acid a probe comprising the sequence set forth in SEQ ID NO: 20 or a sequence complementary to SEQ ID NO: 20.

10. The method of claim 5, wherein the group of primers is selected from (c) the group of primers comprising the sequences set forth in SEQ ID NO: 22, and SEQ ID NO: 23.

11. The method of claim 10, wherein the amplification product has a length of 80 to 95 bp, preferably 85 to 90 bp, more preferably about 88 bp.

12. The method of claim 10, further comprising hybridizing to the nucleic acid a probe comprising the sequence set forth in SEQ ID NO: 24 or a sequence complementary to SEQ ID NO: 24.

13. The method of claim 1, wherein the deletion starts after position chr15:44,962,085 and ends at position chr15: 45,166,582.

14. The method of claim 1, wherein the inversion comprises an inversion of the sequence downstream of the deleted region and follows the deletion.

15. The method of claim 1, wherein the inverted region starts at position chr15:45,166,583 and ends at position chr15:45,304,626.

16. The method of claim 1, wherein the sequence surrounding the end point of the deletion, which is the start point of the inverted region comprises the sequence set forth in SEQ ID NO: 9 or a sequence complementary to SEQ ID NO: 9.

17. The method of claim 1, wherein identifying a chromosomal deletion and inversion event comprises performing polymerase chain reaction (PCR).

18. The method of claim 1, wherein the loss of antigen presentation via MHC class I indicates resistance against immunotherapy.

19. The method of claim 18, wherein the immunotherapy is tumor immunotherapy.

20. The method of claim 6, wherein the amplification product has a length of 160 to 200 bp, preferably 170 to 190 bp, more preferably about 180 bp.

21. The method of claim 1, wherein the amplifying step comprises amplifying a nucleic acid sequence comprising the sequence set forth in SEQ ID NO: 10 and/or a sequence complementary to SEQ ID NO: 10 to generate an amplification product.

22. A method for screening for a genotype for loss of antigen presentation via major histocompatibility complex (MHC) class I, comprising: obtaining a sample containing nucleic acid from a subject, and identifying a chromosomal deletion and inversion event in a chromosome 15, wherein the deletion and inversion event results in the loss of the beta-2-microglobulin (B2M) locus, and wherein the presence of the chromosomal deletion and inversion event indicates that the subject possesses a genotype for loss of antigen presentation via MHC class I, wherein the identifying comprises (i) amplifying a nucleic acid sequence comprising the sequence set forth in SEO ID NO: 9 and/or a sequence complementary to SEO ID NO: 9 to generate an amplification product, (ii) contacting a probe to the amplification product, and (iii) detecting hybridization of the probe to the amplification product, wherein the amplifying step comprises amplifying a nucleic acid sequence comprising the sequence set forth in SEQ ID NO: 11 and/or a sequence complementary to SEQ ID NO: 11 to generate an amplification product.

23. A method for screening for a genotype for loss of antigen presentation via major histocompatibility complex (MHC) class I, comprising: obtaining a sample containing nucleic acid from a subject, and identifying a chromosomal deletion and inversion event in a chromosome 15, wherein the deletion and inversion event results in the loss of the beta-2-microglobulin (B2M) locus, and wherein the presence of the chromosomal deletion and inversion event indicates that the subject possesses a genotype for loss of antigen presentation via MHC class L wherein the identifying comprises i) amplifying a nucleic acid sequence comprising the sequence set forth in SEO ID NO: 9 and/or a sequence complementary to SEO ID NO: 9 to generate an amplification product, (ii) contacting a probe to the amplification product, and (iii) detecting hybridization of the probe to the amplification product, wherein the amplifying step comprises amplifying a nucleic acid sequence comprising the sequence set forth in SEQ ID NO: 12 and/or a sequence complementary to SEQ ID NO: 12 to generate an amplification product.

\* \* \* \* \*

UNITED STATES PATENT AND TRADEMARK OFFICE
CERTIFICATE OF CORRECTION

| | |
|---|---|
| PATENT NO. | : 11,920,194 B2 |
| APPLICATION NO. | : 16/619761 |
| DATED | : March 5, 2024 |
| INVENTOR(S) | : Ugur Sahin et al. |

It is certified that error appears in the above-identified patent and that said Letters Patent is hereby corrected as shown below:

In the Claims

Column 66, Line 8, Claim 22, "MHC class L" should be changed to --MCH class I,--.

Column 66, Line 10, Claim 22, "set forth in SEO ID NO: 9" should be changed to --set forth in SEQ ID NO: 9--.

Column 66, Line 11, Claim 22, "complementary to SEO ID NO: 9" should be changed to --complementary to SEQ ID NO: 9--.

Column 66, Line 28, Claim 23, "MHC class L" should be changed to --MCH class I,--.

Column 66, Line 30, Claim 23, "set forth in SEO ID NO: 9" should be changed to --set forth in SEQ ID NO: 9--.

Column 66, Line 31, Claim 23, "complementary to SEO ID NO: 9" should be changed to --complementary to SEQ ID NO: 9--.

Signed and Sealed this
Eleventh Day of June, 2024

Katherine Kelly Vidal
*Director of the United States Patent and Trademark Office*

SEQUENCE LISTING

<160> NUMBER OF SEQ ID NOS: 26

<210> SEQ ID NO 1
<211> LENGTH: 701
<212> TYPE: DNA
<213> ORGANISM: Homo sapiens

<400> SEQUENCE: 1

```
ccctaaggaa ctgatatctc accttctcaa tccggtataa tacccgaagc ctctgactgc      60
ttgcagcttc tatatcctag gagaagggag tcaccagcta tcagctacac tgccactgcc     120
acagccctag cccaggcccc caactagcta gagattgagc tggaaaggct agaaacaaag     180
tctgatcaca cttcttcctc cttcttcggt cacagtctta aacacaagaa tgttctagac     240
ccttcttcca aagggagag aaaaatgtct gggaagatag tgctcccacc tgctcttgag     300
ttccatgggg taccgcatca atagctcggc gagggctgaa gcatgtcgac acagctacct     360
ggcccaggga accctcgatt cggaccactg catgagaaga gaggcacatt tccttccccc     420
tcccacactc tgtccaccca gatgcccagc ccaagtcagc aggtcagccc tgaccctacc     480
ggactcataa gcctctgcct tcggaatgta aggcgttacc agcttgaggg actcaacccg     540
gtttcttcgt ccaagtagct cttcgtctgc ctgcttcttc tctagcttct ggtaatattc     600
ctgagaatgc acggaatagg aaacaaaaaa acaaacacc ttatattcat cttttgaatt     660
tagaattaag tttctcaagt gcagcctctt aagtttagtt t                         701
```

<210> SEQ ID NO 2
<211> LENGTH: 601
<212> TYPE: DNA
<213> ORGANISM: Homo sapiens

<400> SEQUENCE: 2

| | | | | | |
|---|---|---|---|---|---|
| tctccaagtg | aggtcgaagt | tttgccctag | accctgtagg | acatctatat | acctatcagg | 60 |
| atcatctgaa | aacttcccca | gatctacctt | gatctgcttt | aaatcagaga | gggagaaggg | 120 |
| gacatgtacc | caggttgggc | caaattcccc | tccccctaca | gcttgaaaag | aacataacca | 180 |
| atagcccaga | ggtttttgtg | gccccttgga | gatttctttg | cttgtttcct | tctgggtggg | 240 |
| ggagattaga | ggaggctcat | cattaatagg | aagaggagct | gtagggaggc | taggatatgg | 300 |
| gggtaagctg | agaggtcctc | ctgtggaatg | taggttgcaa | gctttgcata | gttgtggatt | 360 |
| gtccttcagt | gaaaagaaag | cttggacata | aggtatttca | ctccatttgc | cttccatctt | 420 |
| acagaaaaag | tcaagctgca | ggataatact | gtaatttata | cttttccacag | gtggccattt | 480 |
| ttccctatca | gagagagaat | attgggacca | ggccacagtg | cagaaaaaaa | taagcctctt | 540 |
| cttttttcagg | gcttgcaggt | caaattcatc | ccaatggctt | aggatgcatt | tcaagtgtga | 600 |
| g | | | | | | 601 |

<210> SEQ ID NO 3
<211> LENGTH: 601
<212> TYPE: DNA
<213> ORGANISM: Homo sapiens

<400> SEQUENCE: 3

| | | | | | |
|---|---|---|---|---|---|
| ccacctgagg | gacgtataaa | ttacaatagt | atcctgcagc | ttgaactttt | ctgtaagaag | 60 |
| gaaggcaagt | ggagtgaaat | accttatgtc | caagctttct | tttcactgaa | ggacaatcca | 120 |
| caactatgca | aagcttgcaa | tctacattcc | acaggaggac | ctctcagctt | accccccatat | 180 |
| cctagcctcc | ttacagctcc | tcttccttcc | tattaatgat | gagcctcctc | taatctcccc | 240 |
| cacccagaag | gaaacaagca | agaaatctc | caagggacca | caaaaaaccc | gctataggtt | 300 |
| atgtcctctt | caagctgtag | ggggagggga | atttggccca | acccgggtac | aagtcccctt | 360 |
| ctccctctct | gatttaaagc | agatcaagtt | agatctgggg | aagttttcag | gtgatcctga | 420 |
| taggtatata | gatatcctat | ggggtctagg | gcaaaccttc | gacctcactt | ggagagatgt | 480 |
| catgctattg | ttttgttgct | gttgttgttg | ttttgagatg | gagtttcact | ctgttgccca | 540 |
| ggctggagtg | cagtggcaca | atctcagctc | actgcaagct | ccacttcccg | ggttcacacc | 600 |
| a | | | | | | 601 |

<210> SEQ ID NO 4
<211> LENGTH: 700
<212> TYPE: DNA
<213> ORGANISM: Homo sapiens

<400> SEQUENCE: 4

| | | | | | |
|---|---|---|---|---|---|
| ccctaaggaa | ctgatatctc | accttctcaa | tccggtataa | tacccgaagc | ctctgactgc | 60 |
| ttgcagcttc | tatatcctag | gagaagggag | tcaccagcta | tcagctacac | tgccactgcc | 120 |
| acagccctag | cccaggcccc | caactagcta | gagattgagc | tggaaaggct | agaaacaaag | 180 |
| tctgatcaca | cttcttcctc | cttcttcggt | cacagtctta | aacacaagaa | tgttctagac | 240 |
| ccttcttcca | aggggagag | aaaaatgtct | gggaagatag | tgctcccacc | tgctcttgag | 300 |
| ttccatgggg | taccgcatca | atagctcggc | gagggctgaa | gcatgtcgac | acagctacct | 360 |

```
ggcccaggga acccctcgatt cggaccactg catgagaaga aacctatagc gggttttttg    420
tggtcccttg gagatttctt tgcttgtttc cttctgggtg ggggagatta gaggaggctc    480
atcattaata ggaaggaaga ggagctgtaa ggaggctagg atatgggggt aagctgagag    540
gtcctcctgt ggaatgtaga ttgcaagctt tgcatagttg tggattgtcc ttcagtgaaa    600
agaaagcttg gacataaggt atttcactcc acttgccttc cttcttacag aaaagttcaa    660
gctgcaggat actattgtaa tttatacgtc cctcaggtgg                         700

<210> SEQ ID NO 5
<211> LENGTH: 603
<212> TYPE: DNA
<213> ORGANISM: Homo sapiens

<400> SEQUENCE: 5
ctcacacttg aaatgcatcc taagccattg ggatgaattt gacctgcaag ccctgaaaaa     60
gaagaggctt attttttct gcactgtggc ctggtcccaa tattctctct ctgataggga    120
aaaatggcca cctgtggaaa gtataaatta cagtattatc ctgcagcttg acttttctg    180 taagatggaa ggcaaatgga gtgaaatacc ttatgtccaa gctttctttt cactgaagga    240
caatccacaa ctatgcaaag cttgcaacct acattccaca ggaggacctc tcagcttacc    300
ccatgtcctc ttcaagctgt aggggaggg gaatttggcc caacccgggt acaagtcccc    360
ttctccctct ctgatttaaa gcagatcaag ttagatctgg ggaagttttc aggtgatcct    420
gataggtata tagatatcct atggggtcta gggcaaacct tcgacctcac ttggagagat    480
gtcatgctat tgttttgttg ctgttgttgt tgttttgaga tggagtttca ctctgttgcc    540
caggctggag tgcagtggca caatctcagc tcactgcaag ctccacttcc cgggttcaca    600
cca                                                                 603

<210> SEQ ID NO 6
<211> LENGTH: 701
<212> TYPE: DNA
<213> ORGANISM: Homo sapiens
<220> FEATURE:
<221> NAME/KEY: repeat_unit
<222> LOCATION: (401)..(401)
<223> OTHER INFORMATION: Nucleotide repeated n times, wherein n is an
      integer from 0 to 5, preferably 0 or 1

<400> SEQUENCE: 6
ccctaaggaa ctgatatctc accttctcaa tccggtataa tacccgaagc ctctgactgc     60
ttgcagcttc tatatcctag gagaagggag tcaccagcta tcagctacac tgccactgcc    120
acagccctag cccaggcccc caactagcta gagattgagc tggaaaggct agaaacaaag    180
tctgatcaca cttcttcctc cttcttcggt cacagtctta aacacaagaa tgttctagac    240
ccttcttcca agggagag aaaaatgtct gggaagatag tgctcccacc tgctcttgag     300
ttccatgggg taccgcatca atagctcggc gagggctgaa gcatgtcgac acagctacct    360
ggcccaggga accctcgatt cggaccactg catgagaaga aaacctatag cgggttttttt   420 gtggtccctt ggagatttct tgcttgtttt cctctgggt ggggagatt agaggaggct    480 catcattaat aggaaggaag aggagctgta aggaggctag gatatggggg taagctgaga    540
ggtcctcctg tggaatgtag attgcaagct ttgcatagtt gtggattgtc cttcagtgaa    600
aagaaagctt ggacataagg tatttcactc cacttgcctt ccttcttaca gaaaagttca    660
agctgcagga tactattgta atttatacgt ccctcaggtg g                       701
```

-continued

```
<210> SEQ ID NO 7
<211> LENGTH: 177
<212> TYPE: DNA
<213> ORGANISM: Homo sapiens

<400> SEQUENCE: 7
tacagcatgt cgacacagct acctggccca gggaaccctc gattcggacc actgcatgag      60
aagaaaatct atagcgggtt ttttgtggtc ccttggagat ttctttgctt gtttccttct     120
gggtggggga gattcgagga ggctcatcta ttcatagcaa gaacagagcg taatact        177

<210> SEQ ID NO 8
<211> LENGTH: 107
<212> TYPE: DNA
<213> ORGANISM: Homo sapiens

<400> SEQUENCE: 8
ccacccagaa ggaaacaagc aaagaaatct ccaagggacc acaaaaaacc cgctataggt      60
tttcttctca tgcagtggtc cgaatcgagg gttccctggg ccaggta                   107

<210> SEQ ID NO 9
<211> LENGTH: 11
<212> TYPE: DNA
<213> ORGANISM: Homo sapiens
<220> FEATURE:
<221> NAME/KEY: repeat_unit
<222> LOCATION: (6)..(6)
<223> OTHER INFORMATION: Nucleotide repeated n times, wherein n is an
      integer from 0 to 5, preferably 0 or 1

<400> SEQUENCE: 9
aggttttctt c                                                           11

<210> SEQ ID NO 10
<211> LENGTH: 11
<212> TYPE: DNA
<213> ORGANISM: Homo sapiens

<400> SEQUENCE: 10
aggttttctt c                                                           11

<210> SEQ ID NO 11
<211> LENGTH: 21
<212> TYPE: DNA
<213> ORGANISM: Homo sapiens
<220> FEATURE:
<221> NAME/KEY: repeat_unit
<222> LOCATION: (11)..(11)
<223> OTHER INFORMATION: Nucleotide repeated n times, wherein n is an
      integer from 0 to 5, preferably 0 or 1

<400> SEQUENCE: 11
gctataggtt ttcttctcat g                                                21

<210> SEQ ID NO 12
<211> LENGTH: 21
<212> TYPE: DNA
<213> ORGANISM: Homo sapiens

<400> SEQUENCE: 12
gctataggtt ttcttctcat g                                                21
```

<210> SEQ ID NO 13
<211> LENGTH: 41
<212> TYPE: DNA
<213> ORGANISM: Homo sapiens
<220> FEATURE:
<221> NAME/KEY: repeat_unit
<222> LOCATION: (21)..(21)
<223> OTHER INFORMATION: Nucleotide repeated n times, wherein n is an
      integer from 0 to 5, preferably 0 or 1

<400> SEQUENCE: 13
caaaaaaccc gctataggtt ttcttctcat gcagtggtcc g                            41

<210> SEQ ID NO 14
<211> LENGTH: 41
<212> TYPE: DNA
<213> ORGANISM: Homo sapiens

<400> SEQUENCE: 14
caaaaaaccc gctataggtt ttcttctcat gcagtggtcc g                            41

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
agcatgtcga cacagctacc                                                    20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
acctctcagc ttaccccat                                                     20

<210> SEQ ID NO 17
<211> LENGTH: 94
<212> TYPE: DNA
<213> ORGANISM: Homo sapiens

<400> SEQUENCE: 17
ccacccagaa ggaaacaagc aaagaaatct ccaagggacc acaaaaaacc cgctataggt        60
tttcttctca tgcagtggtc cgaatcgagg gttc                                    94

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide

<400> SEQUENCE: 18
gaaccctcga ttcggaccac                                                    20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide

<400> SEQUENCE: 19
ccacccagaa ggaaacaagc                                               20

<210> SEQ ID NO 20
<211> LENGTH: 36
<212> TYPE: DNA
<213> ORGANISM: Artificial Sequence
<220> FEATURE:
<223> OTHER INFORMATION: Oligonucleotide

<400> SEQUENCE: 20
caagggacca caaaaaaccc gctataggtt ttcttc                             36

<210> SEQ ID NO 21
<211> LENGTH: 88
<212> TYPE: DNA
<213> ORGANISM: Homo sapiens

<400> SEQUENCE: 21
caagcaaaga aatctccaag ggaccacaaa aaacccgcta taggttttct tctcatgcag   60
tggtccgaat cgagggttcc ctgggcca                                      88

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide

<400> SEQUENCE: 22
caagcaaaga aatctccaag gga                                           23

<210> SEQ ID NO 23
<211> LENGTH: 17
<212> TYPE: DNA
<213> ORGANISM: Artificial Sequence
<220> FEATURE:
<223> OTHER INFORMATION: Oligonucleotide

<400> SEQUENCE: 23
tggcccaggg aaccctc                                                  17

<210> SEQ ID NO 24
<211> LENGTH: 37
<212> TYPE: DNA
<213> ORGANISM: Artificial Sequence
<220> FEATURE:
<223> OTHER INFORMATION: Oligonucleotide

<400> SEQUENCE: 24
cacaaaaaac ccgctatagg ttttcttctc atgcagt                            37

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
atgcagcgat accagttgct                                               20

-continued

```
<210> SEQ ID NO 26
<211> LENGTH: 20
<212> TYPE: DNA
<213> ORGANISM: Artificial Sequence
<220> FEATURE:
<223> OTHER INFORMATION: Oligonucleotide

<400> SEQUENCE: 26
ggaaagcacc aaatgccgag                                                   20
```